(12) United States Patent
Jain et al.

(10) Patent No.: US 9,216,108 B2
(45) Date of Patent: Dec. 22, 2015

(54) LACRIMAL IMPLANTS AND RELATED METHODS

(75) Inventors: Rachna Jain, Milpitas, CA (US); Robert W. Shimizu, Laguna Niguel, CA (US)

(73) Assignee: Mati Therapeutics Inc., Austin, TX (US)

(*) Notice: Subject to any disclaimer, the term of this patent is extended or adjusted under 35 U.S.C. 154(b) by 347 days.

(21) Appl. No.: 12/378,710

(22) Filed: Feb. 17, 2009

(65) Prior Publication Data

US 2009/0264861 A1 Oct. 22, 2009

Related U.S. Application Data

(60) Provisional application No. 61/066,233, filed on Feb. 18, 2008, provisional application No. 61/049,347, filed on Apr. 30, 2008.

(51) Int. Cl.
*A61M 35/00* (2006.01)
*A61F 9/007* (2006.01)
(Continued)

(52) U.S. Cl.
CPC ............ *A61F 9/00772* (2013.01); *A61M 29/02* (2013.01); *A61M 31/002* (2013.01);
(Continued)

(58) Field of Classification Search
CPC .................... A61F 2210/0061; A61F 9/00772; A61F 9/00781; A61F 9/0017; A61B 17/12022; A61K 9/0051; A61M 29/02; A61M 31/00; A61M 31/02; A61M 2210/0612
USPC .............................................. 604/8, 294, 309
See application file for complete search history.

(56) References Cited

U.S. PATENT DOCUMENTS 3,865,108 A 2/1975 Hartop
3,949,750 A * 4/1976 Freeman ....................... 424/427
(Continued)

FOREIGN PATENT DOCUMENTS

EP 0442745 A1 8/1991
EP 0621022 A1 10/1994
(Continued)

OTHER PUBLICATIONS

"International Application Serial No. PCT/US2009/000963, Invitation to Pay Additional Fees and Partial International Search mailed Jul. 31, 2009", 8 pgs.
(Continued)

*Primary Examiner* — Bhisma Mehta
*Assistant Examiner* — Larry R Wilson
(74) *Attorney, Agent, or Firm* — Koren Anderson; Mati Therapeutics Inc.

(57) ABSTRACT

Lacrimal implants and related methods providing secure retention within the lacrimal punctum of an eye are described. The lacrimal implants can comprise a implant body configured for at least partial insertion through the lacrimal punctum and into a lacrimal canaliculus. The implant body can include a deformable retention structure that can be configured to substantially encapsulate an expandable retention element. In some examples, the expandable retention element can include a fluid absorbing material, which can be exposed to fluid such as via a fluid permeable retainer or a fluid permeable aperture. As the fluid absorbing material retains fluid (i.e., upon acceptance of fluid into the retention structure), its size increases and its shape can change to urge one or more portions of the retention structure outward, such as against a wall of the lacrimal canaliculus, thereby securely retaining the lacrimal implant within the punctum.

29 Claims, 17 Drawing Sheets

(51) Int. Cl.
*A61M 31/00* (2006.01)
*A61M 29/02* (2006.01)
*A61F 9/00* (2006.01)
*A61K 9/00* (2006.01)
*A61B 17/12* (2006.01)

(52) U.S. Cl.
CPC ......... *A61B17/12022* (2013.01); *A61F 9/0017* (2013.01); *A61F 9/00781* (2013.01); *A61F 2210/0061* (2013.01); *A61K 9/0051* (2013.01); *A61M 31/00* (2013.01); *A61M 2210/0612* (2013.01)

(56) References Cited

U.S. PATENT DOCUMENTS

| | | |
|---|---|---|
| 4,014,335 A | 3/1977 | Arnold |
| 4,660,546 A | 4/1987 | Herrick et al. |
| 4,886,488 A | 12/1989 | White |
| 4,915,684 A | 4/1990 | MacKeen et al. |
| 4,959,048 A | 9/1990 | Seder et al. |
| 5,041,081 A | 8/1991 | Odrich |
| 5,049,142 A | 9/1991 | Herrick et al. |
| 5,053,030 A | 10/1991 | Herrick et al. |
| 5,128,058 A | 7/1992 | Ishii et al. |
| 5,133,159 A | 7/1992 | Nelson |
| 5,163,959 A | 11/1992 | Herrick |
| 5,171,270 A | 12/1992 | Herrick |
| 5,283,063 A * | 2/1994 | Freeman ................. 424/427 |
| 5,318,513 A | 6/1994 | Leib |
| 5,334,137 A | 8/1994 | Freeman |
| 5,395,618 A | 3/1995 | Darougar et al. |
| 5,417,651 A | 5/1995 | Guena et al. |
| 5,423,777 A | 6/1995 | Tajiri et al. |
| 5,466,233 A | 11/1995 | Weiner et al. |
| 5,556,633 A | 9/1996 | Haddad et al. |
| 5,707,643 A | 1/1998 | Ogura et al. |
| 5,723,005 A | 3/1998 | Herick |
| 5,766,243 A | 6/1998 | Christensen et al. |
| 5,773,019 A | 6/1998 | Ashton et al. |
| 5,824,073 A | 10/1998 | Peyman |
| 5,826,584 A | 10/1998 | Schmitt |
| 5,830,171 A | 11/1998 | Wallace |
| 5,840,054 A | 11/1998 | Hamano et al. |
| 5,961,370 A | 10/1999 | Valle et al. |
| 5,962,383 A | 10/1999 | Doyel et al. |
| 5,993,407 A | 11/1999 | Moazed |
| 6,010,391 A | 1/2000 | Lewellen et al. |
| 6,016,806 A | 1/2000 | Webb |
| 6,027,470 A | 2/2000 | Mendius |
| 6,041,785 A | 3/2000 | Webb |
| 6,082,362 A | 7/2000 | Webb |
| 6,095,901 A | 8/2000 | Robinson et al. |
| 6,149,684 A | 11/2000 | Herrick |
| 6,196,993 B1 | 3/2001 | Cohan et al. |
| 6,234,175 B1 * | 5/2001 | Zhou et al. .................... 128/887 |
| 6,238,363 B1 | 5/2001 | Kurihashi |
| 6,254,562 B1 | 7/2001 | Fouere |
| 6,264,971 B1 | 7/2001 | Darougar et al. |
| 6,290,684 B1 | 9/2001 | Herrick |
| 6,306,114 B1 | 10/2001 | Freeman et al. |
| 6,331,313 B1 | 12/2001 | Wong et al. |
| 6,371,122 B1 | 4/2002 | Mandelkorn |
| 6,375,972 B1 | 4/2002 | Guo et al. |
| 6,383,192 B1 | 5/2002 | Kurihashi |
| 6,428,502 B1 | 8/2002 | Lang |
| 6,455,062 B1 | 9/2002 | Olejnik et al. |
| 6,605,108 B2 | 8/2003 | Mendius et al. |
| 6,629,533 B1 | 10/2003 | Webb et al. |
| 6,706,275 B1 | 3/2004 | Camp |
| 6,729,939 B2 | 5/2004 | Wrue |
| 6,756,049 B2 | 6/2004 | Brubaker et al. |
| 6,780,164 B2 | 8/2004 | Bergheim et al. |
| 6,840,931 B2 | 1/2005 | Peterson et al. |
| 6,846,318 B2 | 1/2005 | Camp |
| 6,866,563 B2 | 3/2005 | Green |
| 6,964,781 B2 | 11/2005 | Brubaker |
| 6,982,090 B2 | 1/2006 | Gillespie |
| 6,991,808 B2 | 1/2006 | Brubaker et al. |
| 6,994,684 B2 | 2/2006 | Murray et al. |
| 7,017,580 B2 | 3/2006 | Prescott et al. |
| 7,117,870 B2 | 10/2006 | Prescott |
| 7,135,009 B2 | 11/2006 | Tu et al. |
| 7,204,253 B2 | 4/2007 | Mendius et al. |
| 7,204,995 B2 | 4/2007 | El-Sherif et al. |
| 2002/0032400 A1 | 3/2002 | Moazed |
| 2002/0151960 A1 * | 10/2002 | Mendius et al. ............. 623/1.15 |
| 2002/0198453 A1 | 12/2002 | Herrick, II |
| 2003/0130612 A1 | 7/2003 | Moazed |
| 2004/0102729 A1 | 5/2004 | Haffner et al. |
| 2004/0121014 A1 | 6/2004 | Guo et al. |
| 2004/0127843 A1 | 7/2004 | Tu et al. |
| 2004/0141151 A1 | 7/2004 | Gillespie |
| 2004/0147870 A1 | 7/2004 | Burns |
| 2004/0175410 A1 * | 9/2004 | Ashton et al. ................. 424/427 |
| 2004/0249333 A1 | 12/2004 | Bergheim et al. |
| 2004/0265356 A1 | 12/2004 | Mosack |
| 2005/0095269 A1 | 5/2005 | Ainpour et al. |
| 2005/0181018 A1 * | 8/2005 | Peyman ....................... 424/427 |
| 2005/0197614 A1 | 9/2005 | Pritchard et al. |
| 2005/0220882 A1 | 10/2005 | Pritchard et al. |
| 2005/0232972 A1 | 10/2005 | Odrich et al. |
| 2005/0244469 A1 | 11/2005 | Whitcup et al. |
| 2005/0266047 A1 | 12/2005 | Tu et al. |
| 2005/0271704 A1 | 12/2005 | Tu et al. |
| 2005/0283109 A1 | 12/2005 | Peyman |
| 2006/0013835 A1 | 1/2006 | Anderson et al. |
| 2006/0020248 A1 | 1/2006 | Prescott |
| 2006/0020253 A1 | 1/2006 | Prescott |
| 2006/0074370 A1 | 4/2006 | Zhou |
| 2006/0106352 A1 | 5/2006 | Kurihashi |
| 2006/0122553 A1 | 6/2006 | Hanna |
| 2007/0083146 A1 | 4/2007 | Murray |
| 2007/0123924 A1 | 5/2007 | Becker |
| 2007/0132125 A1 | 6/2007 | Rastogi et al. |
| 2007/0135914 A1 | 6/2007 | Herrick, II |
| 2007/0243230 A1 * | 10/2007 | de Juan et al. ................. 424/427 |
| 2007/0269487 A1 | 11/2007 | de Juan et al. |
| 2007/0298075 A1 * | 12/2007 | Borgia et al. ................. 424/428 |
| 2007/0299515 A1 | 12/2007 | Herrick, II |
| 2007/0299516 A1 | 12/2007 | Cui |
| 2008/0038317 A1 | 2/2008 | Chang et al. |
| 2008/0045878 A1 | 2/2008 | Bergheim et al. |
| 2008/0045911 A1 | 2/2008 | Borgia et al. |

FOREIGN PATENT DOCUMENTS

| | | |
|---|---|---|
| JP | 10-33584 A | 2/1998 |
| JP | 2004-202276 A | 7/2004 |
| JP | 2005-628 A | 1/2005 |
| JP | 2005-58622 A | 3/2005 |
| JP | 2005-110765 A | 4/2005 |
| JP | 2005-110930 A | 4/2005 |
| JP | 2005-312835 A | 11/2005 |
| JP | 2005-319190 A | 11/2005 |
| JP | 2005-328922 A | 12/2005 |
| JP | 2007195819 A | 8/2007 |
| WO | WO-98/33461 A1 | 8/1998 |
| WO | WO-98/42282 A1 | 10/1998 |
| WO | WO-99/37260 A1 | 7/1999 |
| WO | WO-99/44553 A1 | 9/1999 |
| WO | WO-99/64089 A1 | 12/1999 |
| WO | WO-99/65544 A1 | 12/1999 |
| WO | WO-00/27321 A1 | 5/2000 |
| WO | WO-00/62760 A1 | 10/2000 |
| WO | WO-02/11783 A1 | 2/2002 |
| WO | WO-02/083198 A2 | 10/2002 |
| WO | WO-03/017897 A2 | 3/2003 |
| WO | WO-03/057101 A1 | 7/2003 |
| WO | WO-2004/004614 A2 | 1/2004 |
| WO | WO-2004/024043 A2 | 3/2004 |
| WO | WO-2004/105658 A1 | 12/2004 |
| WO | WO-2004/112639 A2 | 12/2004 |
| WO | WO-2005/000154 A2 | 1/2005 |

(56) References Cited

FOREIGN PATENT DOCUMENTS

| WO | WO-2005/086694 A2 | 9/2005 |
|---|---|---|
| WO | WO-2006/014434 A2 | 2/2006 |
| WO | WO-2006/031658 A2 | 3/2006 |
| WO | WO-2006/044669 A2 | 4/2006 |
| WO | WO-2006/096586 A1 | 9/2006 |
| WO | WO-2007/008262 A2 | 1/2007 |
| WO | WO 2007/115259 A2 | 10/2007 |
| WO | WO-2007/115261 A2 | 10/2007 |
| WO | WO-2007/149771 A2 | 12/2007 |
| WO | WO-2007/149832 A2 | 12/2007 |
| WO | WO-2008/056060 A2 | 5/2008 |

OTHER PUBLICATIONS

"International Application Serial No. PCT/US2008/010479, International Search Report mailed Dec. 15, 2008", 6 pgs.

"International Application Serial No. PCT/US2008/010479, Written Opinion mailed Dec. 15, 2008", 7 pgs.

De Juan, Jr., E., et al., "Expandable Nasolacrimal Drainage System Implants", U.S. Appl. No. 60/970,696, filed Sep. 7, 2007, 82 pgs.

De Juan, Jr., E., et al., "Manufacture of Expandable Nasolacrimal Drainage System Implants", U.S. Appl. No. 60/970,720, filed Sep. 7 2007, 57 pgs.

Jain, R., et al., "Lacrimal Implants and Related Methods", U.S. Appl. No. 61/066,233, filed Feb. 18, 2008, 133 pgs.

International Search Report and Written Opinion as issued for PCT/US2009/000963, dated Apr. 15, 2010.

International Preliminary Report on Patentability as issued for PCT/US2009/000963, dated Sep. 2, 2010.

Machine-Generated English Translation of PCT Publication No. WO 03/057101 A1, Dated: Jul. 17, 2003.

* cited by examiner

EXAMPLE OF A METHOD OF MANUFACTURING

EXAMPLE OF A METHOD OF TREATING AN EYE

LACRIMAL IMPLANTS AND RELATED METHODS

CLAIM OF PRIORITY

This non-provisional application claims the benefit of priority under 35 U.S.C. §119(e) to U.S. Provisional Patent Application Ser. No. 61/066,233 filed on Feb. 18, 2008 and U.S. Provisional Patent Application Ser. No. 61/049,347 filed on Apr. 30, 2008, the specifications of which are herein incorporated by reference in their entirety.

TECHNICAL FIELD

This patent document pertains generally to ocular implants. More particularly, but not by way of limitation, this patent document pertains to lacrimal implants (e.g., punctum plugs), methods of making such implants, and methods of treating ocular diseases using such implants.

BACKGROUND

A variety of challenges face patients and physicians in the area of ocular disease management, including drug delivery to the eyes and treatment of dry eyes. Dry eye, including keratoconjunctivitis sicca, is a common ocular condition that can require therapy. Dry eye has been experienced by a broad demographic band, and is common in elderly individuals. A variety of current treatment modalities target physiological conditions that contribute to dry eye, including augmentation of normal tear fluid, enhancement of tear film component production, and methods to enhance the residence time of tears, such as blocking the tear flow from an eye into and through a lacrimal canaliculus.

Many current tear flow blockage techniques have drawbacks, including being irreversible in nature. For instance, some tear flow blockage techniques involve closing the canalicular canal by stitching the punctal opening shut or by using electrical or laser cauterization to seal the punctal opening. Although such procedures can provide the desired result of blocking tear flow to treat a dry eye, they are unfortunately not reversible without reconstructive surgery.

In addition to dry eye symptom relief, a variety of challenges face patients and physicians in the area of ocular disease or disorder management, including adequate drug or other therapeutic agent delivery to the eyes. In ocular management, for example, many current ocular drug delivery systems require repetitive manual administration and are often ineffective due to a lack of patient compliance or inadequate drug concentrations reaching the eye.

In order to treat eye infection, inflammation of an eye, glaucoma and other ocular diseases or disorders, drugs or other therapeutic agents are often required to be administered to the eye. A conventional method of drug delivery is by topical drop application to the eye's surface. Topical eye drops, though effective, can be inefficient. As one example, when an eye drop is instilled in an eye, it often overfills the conjunctival sac (i.e., the pocket between the eye and the lids) causing a substantial portion of the drop to be lost due to overflow of the lid margin and spillage onto the cheek. In addition, a large portion of the drop remaining on the ocular surface can be washed away into and through a lacrimal canaliculus, thereby diluting the concentration of the drug before it can absorbingly treat the eye. Moreover, topically applied drugs often have a peak ocular effect for about two hours post-application, after which additional applications of the drugs should be, but are often not, administered to maintain the desired drug therapeutic benefit.

To compound ocular management difficulty, patients often do not use their eye drops as prescribed. This poor compliance can be due to, for example, an initial stinging or burning sensation caused by the eye drop and experience by a patient. Instilling eye drops in one's own eye can be difficult, in part because of the normal reflex to protect the eye. Therefore, one or more drops may miss the eye. Older patients may have additional problems instilling drops due to arthritis, unsteadiness, and decreased vision. Pediatric and psychiatric populations pose difficulties as well.

EXEMPLARY ASPECTS AND EMBODIMENTS OF THE INVENTION

The present inventors have recognized various promising techniques to increase the residence time of tears on an eye and delivery of drug or other therapeutic agent to the eye. These techniques can include placing a removable, and optionally drug releasing, lacrimal implant through a lacrimal punctum and into the associated canaliculus. It is believed that by allowing for the sustained release of a drug, the present lacrimal implants can overcome some of the drawbacks associated with topical drop administration, such as poor patient compliance, waste or untimely application. One promising approach to successful blocking of tear flow from the eye is to place a removable lacrimal implant into the lacrimal punctum.

The present inventors have further recognized that the lacrimal implant should have one or more of the ability to be easily implanted and removed without much biasing of the lacrimal punctum or the associated lacrimal canaliculus, should be securely retainable in the lacrimal punctum upon implantation, and, when made and used as a drug delivery system, should allow for the sustained release of drugs at a desired therapeutic level for an extended period of time.

Lacrimal implants for treating diseases or disorders are disclosed. More particularly, lacrimal implants, methods of making such implants, and methods of treating ocular diseases or disorders using such implants are disclosed. To better illustrate the subject matter described herein, a non-limiting list of exemplary aspects and embodiments is provided here.

1. A lacrimal implant insertable through a lacrimal punctum, the lacrimal implant comprising:
    a implant body including a retention structure, the retention structure having a fluid permeable retainer;
    a hydrogel retention element substantially encapsulated by the retention structure, the hydrogel retention element configured to expand when the retention structure is implanted in a lacrimal canaliculus; and
    wherein the fluid permeable retainer allows fluid permeation into the retention structure, and further inhibits the hydrogel retention element during expansion from protruding out of the retention structure.
2. The lacrimal implant according to aspect 1, wherein the retention structure includes at least one chamber into which the hydrogel retention element is disposed.
3. The lacrimal implant according to any of aspects 1 or 2, wherein at least a portion of the implant body is configured to remain outside of the lacrimal punctum.
4. The lacrimal implant according to any of aspects 1 or 2, wherein the implant body is configured to be completely insertable through the lacrimal punctum.
5. The lacrimal implant according to any of aspects 1-4, wherein the fluid permeable retainer inhibits at least 80% of the expanded hydrogel retention element from protruding out of the retention structure.

6. The lacrimal implant according to any of aspects 1-5, wherein the fluid permeable retainer includes a fluid permeable portion comprising at least about 50 wt. % silicone in combination with at least one hydrophilic polymer selected from the group consisting of: a contact lens material, sodium chloride, polyethylene oxide, polyethylene glycol, polyvinyl pyrilidone, polyvinyl alcohol, and any combination thereof.

7. The lacrimal implant according to aspect 6, wherein the fluid permeable retainer includes at least about 80 wt. % silicone.

8. The lacrimal implant according to aspect 6, wherein the fluid permeable retainer includes about 60 wt. % silicone and about 40 wt. % sodium chloride.

9. The lacrimal implant according to aspect 6, wherein the fluid permeable retainer includes about 70 wt. % silicone and about 30 wt. % polyvinyl pyrilidone.

10. The lacrimal implant according to aspect 6, wherein the fluid permeable retainer includes about 75% silicone and about 25% polyethylene oxide.

11. The lacrimal implant according to aspect 6, wherein the fluid permeable retainer includes about 80% silicone and about 20% contact lens material.

12. The lacrimal implant according to aspect 6, wherein the contact lens material comprises at least one of a hydrogel, a 2hydroxyethyl methacrylate (HEMA) copolymer, or a poly(methyl methacrylate) (PMMA) copolymer.

13. The lacrimal implant according to any of aspects 1-12, wherein the hydrogel retention element comprises at least one of polyurethane or silicone.

14. The lacrimal implant according to any of aspects 1-13, wherein the hydrogel retention element comprises an expansion capacity of up to 1 time its unexpanded volume.

15. The lacrimal implant according to any of aspects 1-13, wherein the hydrogel retention element comprises an expansion capacity of up to 10 times its unexpanded volume.

16. The lacrimal implant according to any of aspects 1-13, wherein the hydrogel retention element comprises an expansion capacity of up to 100 times its unexpanded volume.

17. The lacrimal implant according to any of aspects 1-16, wherein the implant body is configured such that an outer surface portion of the implant body is deformable outward upon expansion of the hydrogel retention element.

18. The lacrimal implant according to aspect 17, wherein the implant body includes an elastic material comprising at least one of silicone, polyurethane, or an acrylic.

19. The lacrimal implant according to any of aspects 1-18, comprising a implant body projection extending at least partially from or around a proximal end portion of the implant body, and configured to seat against the lacrimal punctum.

20. The lacrimal implant according to aspect 19, wherein the proximal end portion of the projection includes a convex-shape.

21. The lacrimal implant according to any of aspects 1-20, comprising a fluid swellable material disposed on an outer surface portion of the implant body, the fluid swellable material providing secondary expansion of the implant body when located in the lacrimal canaliculus.

22. The lacrimal implant according to any of aspects 1-21, wherein the length of the retention structure is at least about one fifth the length of the implant body.

23. The lacrimal implant according to any of aspects 1-21, wherein the length of the retention structure is at least about one fourth the length of the implant body.

24. The lacrimal implant according to any of aspects 1-21, wherein the length of the retention structure is at least about one third the length of the implant body.

25. The lacrimal implant according to any of aspects 1-21, wherein the length of the retention structure is at least about one half the length of the implant body.

26. The lacrimal implant according to any of aspects 1-21, wherein the length of the retention structure is at least about three quarters the length of the implant body.

27. The lacrimal implant according to any of aspects 1-21, wherein the length of the retention structure is about equal to the length of the implant body.

28. A lacrimal implant insertable through a lacrimal punctum for delivering a release of an agent to an eye, the lacrimal implant comprising:
a implant body extending from a proximal end portion to a distal end portion, the implant body including a drug core at or near the proximal end portion and a retention structure at or near the distal end portion,
the drug core comprising an agent and having at least one surface providing release of the agent to the eye,
the retention structure having a fluid permeable retainer and substantially encapsulating a hydrogel retention element, the hydrogel retention element configured to expand when the retention structure is in a lacrimal canaliculus; and
wherein the fluid permeable retainer allows fluid permeation into the retention structure, and further inhibits the hydrogel retention element during expansion from protruding out of the retention structure.

29. The lacrimal implant according to aspect 28, wherein the implant body includes a first chamber configured to house the drug core and a second chamber configured to house the hydrogel retention element, the second chamber disposed distal of the first chamber.

30. The lacrimal implant according to any of aspects 28 or 29, wherein the drug core includes at least one therapeutic agent inclusion distributed in a solid matrix and at least partially covered by a sheath body to define at least one exposed drug core surface.

31. The lacrimal implant according to aspect 30, wherein the at least one drug core surface is disposed near the proximal end portion of the implant body to contact a tear fluid and release the therapeutic agent over a sustained period when the implant body is inserted in the lacrimal punctum.

32. The lacrimal implant according to any of aspects 28-31, wherein the drug core and the retention structure are moldable together to form a single piece.

33. The lacrimal implant according to any of aspects 28-31, wherein the drug core is formed as a single first piece and the retention structure is formed as a single second piece, the first piece couplable to the second piece.

34. The lacrimal implant according to any of aspects 28-33, wherein the fluid permeable retainer includes a fluid permeable portion comprising at least about 50 wt. % silicone in combination with at least one hydrophilic polymer selected from the group consisting of: a contact lens material, sodium chloride, polyethylene oxide, polyethylene glycol, polyvinyl pyrilidone, polyvinyl alcohol, and any combination thereof.

35. The lacrimal implant according to any of aspects 28-34, wherein the proximal end portion of the implant body including the drug core comprises a first material, and the distal end portion of the implant body including the retention structure comprises a second material different from the first material.

36. The lacrimal implant according to any of aspects 28-35, comprising a implant body projection extending at least partially from the implant body at a position near the proximal end portion, the implant body projection configured to seat against the punctum.

37. The lacrimal implant according to any of aspects 28-36, comprising a implant body septum positioned between the drug core and the hydrogel retention element, the septum preventing communication of a material between the drug core and the hydrogel retention element.

38. The lacrimal implant according to any of aspects 28-37, comprising a fluid swellable material disposed on an outer surface portion of the implant body, the fluid swellable material providing secondary expansion of the implant body when located in the lacrimal canaliculus.

39. A lacrimal implant insertable through a lacrimal punctum, the lacrimal implant comprising:
a implant body including a retention structure, the retention structure having a fluid permeable aperture;
a hydrogel retention element substantially encapsulated by the retention structure, the hydrogel retention element configured to expand when the retention structure is in a lacrimal canaliculus; and
wherein the fluid permeable aperture has a size and shape allowing fluid into the retention structure, and further inhibiting the hydrogel retention element during expansion from protruding out of the retention structure.

40. The lacrimal implant according to aspect 39, wherein the size and shape of the fluid permeable aperture inhibits the escape of the hydrogel retention element such that expulsion thereof is limited to less than 10% of an expanded hydrogel retention element volume.

41. The lacrimal implant according to any of aspects 39 or 40, wherein the size and shape of the fluid permeable aperture inhibits the escape of the hydrogel retention element such that expulsion thereof is limited to less than 5% of an expanded hydrogel retention element volume.

42. The lacrimal implant according to any of aspects 39-41, wherein the size and shape of the fluid permeable aperture inhibits the escape of the hydrogel retention element such that expulsion thereof is limited to less than 1% of an expanded hydrogel retention element volume.

43. The lacrimal implant according to any of aspects 39-42, wherein the size and shape of the fluid permeable aperture precludes the escape of the hydrogel retention element in both its initial dry state and its expanded hydrated state.

44. The lacrimal implant according to any of aspects 39-43, wherein the size and shape of the fluid permeable aperture comprises a diameter up to about 0.3 millimeters.

45. The lacrimal implant according to any of aspects 39-44, comprising a non-permeable, non-hydrophilic cap member coupled to a distal end portion of the implant body.

46. The lacrimal implant according to any of aspects 39-45, comprising an aperture membrane configured to cover the fluid permeable aperture, the aperture membrane disposed on an interior or exterior of the retention structure and having a molecular weight of 10,000 daltons or less.

47. A lacrimal implant insertable into a lacrimal punctum for delivering a release of an agent to an eye, the lacrimal implant comprising:
a implant body extending from a proximal end portion to a distal end portion, the implant body including a drug core at or near the proximal end portion and a retention structure at or near the distal end portion, the drug core comprising at least one surface providing release of the agent to the eye, the retention structure having a fluid permeable aperture;
a hydrogel retention element substantially encapsulated by the retention structure, the hydrogel retention element configured to expand when the retention structure is in a lacrimal canaliculus; and
wherein the fluid permeable aperture has a size and shape allowing fluid into the retention structure, and further inhibiting the hydrogel retention element during expansion from protruding out of the retention structure.

48. The lacrimal implant according to aspect 47, wherein the size and shape of the fluid permeable aperture comprises a diameter up to about 0.30 millimeters.

49. The lacrimal implant according to any of aspects 47 or 48, comprising a non-permeable, non-hydrophilic cap member coupled to a distal end portion of the implant body.

50. The lacrimal implant according to any of aspects 47-49, comprising an aperture membrane configured to cover the fluid permeable aperture, the aperture membrane disposed on an interior or exterior of the retention structure and having a molecular weight of 10,000 daltons or less.

51. The lacrimal implant according to any of aspects 47-50, comprising a implant body septum positioned between the drug core and the hydrogel retention element, the septum preventing communication of a material between the drug core and the hydrogel retention element.

52. A lacrimal implant insertable into a lacrimal punctum, the lacrimal implant comprising:
a implant body extending from a proximal end portion to a distal end portion, the implant body having a retention structure including a fluid permeable or hydrophilic cap member coupled to the distal end portion of the implant body;
a hydrogel retention element substantially encapsulated by the retention structure, the hydrogel retention element configured to expand when the retention structure is in a lacrimal canaliculus; and
wherein the cap member allows fluid permeation into the retention structure, and further inhibits the hydrogel retention element during expansion from protruding out of the retention structure.

53. The lacrimal implant according to aspect 52, wherein the cap member includes at least about 50 wt. % silicone in combination with at least one hydrophilic polymer selected from the group consisting of: a contact lens material, sodium chloride, polyethylene oxide, polyethylene glycol, polyvinyl pyrilidone, polyvinyl alcohol, and any combination thereof.

54. The lacrimal implant according to any of aspects 52 or 53, wherein the cap member includes a tapered distal tip portion to facilitate atraumatic insertion into the lacrimal punctum.

55. The lacrimal implant according to any of aspects 52-54, wherein the cap member covers only a distal end of the retention structure.

56. The lacrimal implant according to aspect 55, wherein the cap member is flush with the distal end of the retention structure.

57. The lacrimal implant according to aspect 55, wherein the cap member is at least partially recessed into an inner wall of the retention structure.

58. The lacrimal implant according to any of aspects 52-54, wherein the cap member covers a distal end and lateral surface of the retention structure.

59. A lacrimal implant insertable into a lacrimal punctum for delivering a release of an agent to an eye, the lacrimal implant comprising:

a implant body extending from a proximal end portion to a distal end portion, the implant body including a drug core at or near the proximal end portion and a retention structure at or near the distal end portion, the drug core comprising at least one surface providing release of the agent to the eye, and the retention structure including a fluid permeable or hydrophilic cap member coupled to the distal end portion of the implant body;

a hydrogel retention element substantially encapsulated by the retention structure, the hydrogel retention element configured to expand when the retention structure is in a lacrimal canaliculus; and wherein the cap member allows fluid movement into the retention structure, and further inhibits the hydrogel retention element during expansion from protruding out of the retention structure.

60. The lacrimal implant according to aspect 59, comprising a implant body projection extending at least partially around the at least one surface of the drug core, the projection including a convex proximal end portion.

61. The lacrimal implant according to any of aspects 59 or 60, comprising a implant body septum positioned between the drug core and the hydrogel retention element, the septum preventing communication of a material between the drug core and the hydrogel retention element.

62. A lacrimal implant insertable into a lacrimal punctum, the lacrimal implant comprising:

a implant body including a retention structure, at least a portion of the retention structure composed of a fluid permeable or hydrophilic material;

a hydrogel retention element substantially encapsulated by the retention structure, the hydrogel retention element configured to expand when the retention structure is in a lacrimal canaliculus; and wherein the retention structure portion composed of the fluid permeable or hydrophilic material allows fluid permeation into the retention structure, and further inhibits the hydrogel retention element during expansion from protruding out of the retention structure.

63. The lacrimal implant according to aspect 62, wherein the fluid permeable or hydrophilic material includes at least about 50 wt. % silicone in combination with at least one hydrophilic polymer selected from the group consisting of: a contact lens material, sodium chloride, polyethylene oxide, polyethylene glycol, polyvinyl pyrilidone, polyvinyl alcohol, and any combination thereof.

64. The lacrimal implant according to any of aspects 62 or 63, wherein the fluid permeable or hydrophilic material includes a hydrogel.

65. The lacrimal implant according to any of aspects 62-64, wherein the retention structure composed of the fluid permeable or hydrophilic material is disposed at a lateral surface exposable to fluid when the retention structure is in the lacrimal canaliculus.

66. The lacrimal implant according to aspect 65, wherein the retention structure composed of the fluid permeable or hydrophilic material accounts for about 5% to about 50% of a total lateral surface area of the retention structure.

67. The lacrimal implant according to aspect 65, wherein the retention structure composed of the fluid permeable or hydrophilic material accounts for greater than 50% of a total lateral surface area of the retention structure.

68. The lacrimal implant according to aspect 65, wherein the retention structure composed of the fluid permeable or hydrophilic material accounts for about 100% of a total lateral surface area of the retention structure.

69. The lacrimal implant according to any of aspects 62-68, wherein the retention structure includes a fluid permeable or hydrophilic cap member coupled to a distal end portion of the implant body.

70. A lacrimal implant insertable into a lacrimal punctum for delivering a release of an agent to an eye, the lacrimal implant comprising:

a implant body extending from a proximal end portion to a distal end portion, the implant body including a drug core at or near the proximal end portion and a retention structure at least partially composed of a fluid permeable or hydrophilic material near the distal end portion, the drug core comprising at least one surface providing release of the agent to the eye;

a hydrogel retention element substantially encapsulated by the retention structure, the hydrogel retention element configured to expand when the retention structure is in a lacrimal canaliculus; and wherein the fluid permeable or hydrophilic material portion of the retention structure allows fluid permeation into the retention structure, and further inhibits the hydrogel retention element during expansion from protruding out of the retention structure.

71. The lacrimal implant according to aspect 70, wherein the retention structure includes a fluid permeable or hydrophilic cap member coupled to the distal end portion of the implant body.

72. The lacrimal implant according to any of aspects 70 or 71, wherein the proximal end portion of the implant body includes a non-permeable and non-hydrophilic material.

73. The lacrimal implant according to any of aspects 70-72, comprising a implant body projection extending at least partially around the at least one surface of the drug core, the projection including a convex proximal end portion.

74. The lacrimal implant according to any of aspects 70-73, comprising a implant body septum positioned between the drug core and the hydrogel retention element, the septum preventing communication of a material between the drug core and the hydrogen retention element.

75. A lacrimal implant insertable into a lacrimal punctum, the lacrimal implant comprising:

a implant body including a retention structure;

a non-fluid-absorbing retention element fully substantially encapsulated by the retention structure, the non-fluid-absorbing retention element configured to expand when the retention structure is in a lacrimal canaliculus; and wherein the retention structure inhibits the non-fluid-absorbing retention element during expansion from protruding out of the retention structure.

76. The lacrimal implant according to aspect 75, wherein the non-fluid-absorbing retention element includes a shape-memory thermoplastic.

77. The lacrimal implant according to aspect 76, wherein the shape-memory thermoplastic is urethane-based.

78. The lacrimal implant according to aspect 75, wherein the non-fluid-absorbing retention element includes an oxide generating system, wherein the oxide generating system is configured to generate and release a plurality of oxides within the retention structure upon insertion into the lacrimal punctum.

79. The lacrimal implant according to any of aspects 75-78, wherein the retention structure includes at least one chamber into which the non-fluid-absorbing retention element is disposed.

80. The lacrimal implant according to any of aspects 75-79, comprising a implant body projection extending at least partially from or around a proximal end portion of the implant body, and configured to seat against the punctum.

81. The lacrimal implant according to aspect 80, wherein the proximal end portion of the projection includes a convex-shape.
82. The lacrimal implant according to any of aspects 75-81, comprising a fluid swellable material disposed on an outer surface portion of the implant body, the fluid swellable material providing secondary retention of the implant body.
83. A lacrimal implant insertable into a lacrimal punctum for delivering a release of an agent to an eye, the lacrimal implant comprising:
a implant body extending from a proximal end portion to a distal end portion, the implant body including a drug core at or near the proximal end portion and a retention structure at or near the distal end portion, the drug core comprising at least one surface providing release of the agent to the eye;
a non-fluid-absorbing retention element fully encapsulated by the retention structure, the non-fluid-absorbing retention element configured to expand when the retention structure is in a lacrimal canaliculus; and
wherein the retention structure inhibits the non-fluid-absorbing retention element during expansion from protruding out of the retention structure.
84. The lacrimal implant according to aspect 83, wherein the implant body includes a first chamber configured to house the drug core and a second chamber configured to house the non-fluid-absorbing retention element, the second chamber disposed distal of the first chamber.
85. The lacrimal implant according to any of aspects 83 or 84, comprising a implant body projection extending at least partially around the at least one surface of the drug core on a proximal end of the implant body.
86. The lacrimal implant according to any of aspects 83-85, comprising a implant body septum positioned between the drug core and the non-fluid-absorbing retention element, the septum preventing communication of a material between the drug core and the non-fluid-absorbing retention element.
87. The lacrimal implant according to any of aspects 83-86, wherein the proximal end portion of the implant body including the drug core comprises a first material, and the distal end portion of the implant body including the non-fluid-absorbing retention structure comprises a second material different from the first material.
88. A kit for treating an eye disease, comprising:
the lacrimal implant according to aspect 1, 28, 39, 47, 52, 59, 62, 70, 75, or 83; and
instructions for using the lacrimal implant to treat the eye disease.
89. A kit for treating an eye disease, comprising:
the lacrimal implant according to aspect 1, 28, 39, 47, 52, 59, 62, 70, 75, or 83;
instructions for using the lacrimal implant to treat the eye disease; and
wherein the lacrimal implant is individually packaged for a single use.
90. A method of manufacturing a lacrimal implant insertable into a lacrimal punctum, the method comprising:
forming a implant body including a retention structure, including forming a fluid permeable retainer through a portion of the retention structure;
substantially encapsulating a hydrogel retention element using the retention structure, the hydrogel retention element configured to expand when the retention structure is in a lacrimal canaliculus; and
wherein forming the fluid permeable retainer includes forming a structure allowing fluid permeation into the retention structure, and which further inhibits the hydrogel retention element during expansion from protruding out of the retention structure.
91. The method according to aspect 90, wherein substantially encapsulating the hydrogel retention element includes disposing the hydrogel retention element in at least one chamber of the retention structure.
92. The method according to any of aspects 90 or 91, wherein substantially encapsulating the hydrogel retention element includes confining the hydrogel retention element within an outer surface boundary of the implant body.
93. The method according to any of aspects 90-92, wherein forming the fluid permeable retainer includes forming a fluid permeable aperture, the aperture having a size and shape inhibiting escape of the hydrogel retention element from the retention structure.
94. The method according to any of aspects 90-93, wherein forming the fluid permeable retainer includes forming a fluid permeable or hydrophilic cap member couplable to a distal end portion of the implant body.
95. The method according to aspect 94, wherein forming the fluid permeable or hydrophilic cap member includes combining at least about 50 wt. % silicone with at least one of a contact lens material, sodium chloride, polyethylene oxide, polyethylene glycol, polyvinyl pyrilidone, or polyvinyl alcohol.
96. The method according to any of aspects 90-95, wherein forming the fluid permeable retainer includes forming a fluid permeable or hydrophilic implant body portion.
97. The method according to aspect 96, wherein the fluid permeable or hydrophilic implant body portion includes at least about 50 wt. % silicone in combination with at least one of a contact lens material, sodium chloride, polyethylene oxide, polyethylene glycol, polyvinyl pyrilidone, or polyvinyl alcohol.
98. The method according to any of aspects 90-97, wherein forming the implant body includes injection molding a first implant body portion using a non-permeable, non-hydrophilic elastic material and injection molding a second implant body portion using, at least in part, a fluid permeable or hydrophilic elastic material.
99. The method according to any of aspects 90-98, wherein forming the implant body includes molding a implant body projection having a diametrical size greater than a size of the punctum and having a convex proximal end portion.
100. The method according to any of aspects 90-99, comprising disposing a drug core in a proximal end portion of the implant body, including positioning the drug core to provide release of the agent via a drug elution port.
101. The method according to any of aspects 90-100, wherein forming the implant body includes molding a implant body septum between the drug core and the retention structure.
102. The method according to any of aspects 90-101, comprising forming the expandable hydrogel retention element, including forming a hydrogel retention element configured to expand to the retaining size and shape in a time period of about 1 minute to about 60 minutes.
103. The method according to any of aspects 90-102, comprising surface treating an outer surface portion of the implant body for adhesion of a fluid swellable material thereto.
104. The method according to aspect 103, wherein surface treating the outer surface portion of the implant body includes plasma treating the implant body portion.
105. The method according to any of aspects 103 or 104, comprising coating an outer surface portion of the implant body with the fluid swellable material.

106. The method according to any of aspects 90-105, comprising pre-stressing a portion of the implant body to direct expansion of the hydrogel retention element.
107. The method according to aspect 106, wherein the pre-stressed portion of the implant body directs expansion of the hydrogel retention element substantially perpendicular to an axis of the implant body.
108. The method according to any of aspects 90-107, comprising controlling an amount of swelling of the hydrogel retention element, including varying the ratio of hydrogel to the ratio of polyurethane or silicone.
109. A method of treating a subject having an eye disorder, comprising:
   inserting a lacrimal implant into at least one lacrimal punctum of the subject, the lacrimal implant comprising,
      a implant body extending from a proximal end portion to a distal end portion, the implant body including a drug core near the proximal end portion and a retention structure at or near the distal end portion,
      the drug core comprising an agent and having at least one surface providing release of the agent to the eye,
      the retention structure having a fluid permeable retainer and substantially encapsulating a hydrogel retention element, the hydrogel retention element configured to expand when the retention structure is in a lacrimal canaliculus; and
      wherein the fluid permeable retainer allows fluid permeation into the retention structure, and further inhibits the hydrogel retention element during expansion from protruding out of the retention structure.
110. A method of treating a subject having an eye disorder, comprising inserting a lacrimal implant according to at least one according to aspects 47, 59, 70, or 83 into at least one lacrimal punctum of the subject.
111. The method according to any of aspects 109 or 110, wherein the subject is a human being.
112. The method according to any of aspects 109 or 110, wherein the eye disorder is glaucoma disease.
113. The method according to aspect 112, wherein the glaucoma disease is ocular hypertension or primary open angle glaucoma.
114. The method according to aspect 113, wherein the agent is an anti-glaucoma medication.
115. The method according to any of aspects 109 or 110, wherein the eye disorder is related to an allergy.
116. The method according to aspect 115, wherein replacing the lacrimal implant is repeated twice per year.
117. The method according to any of aspects 109 or 110, wherein inserting the lacrimal implant is partially through the punctum leaving the most proximal end portion of the implant body exterior of the punctum.
118. The method according to any of aspects 109 or 110, comprising replacing the lacrimal implant that has been inserted with a second lacrimal implant having the same, lower or higher dosage of the agent following an interval of time.
119. The method according to aspect 118, wherein the interval of time is at least 1 month.
120. The method according to any of aspects 118 or 119, wherein replacing the lacrimal implant is repeated for at least two, three, four or five times.
121. The method according to any of aspects 118-120, wherein replacing the lacrimal implant is repeated until the subject no longer requires treating.
122. The method according to any of aspects 109-121, wherein the period of time over which the agent is released is at least one week, at least one month, or at least three months.
123. The method according to any of aspects 109-122, wherein releasing the agent onto the eye includes providing sustained release of the agent onto the eye.
124. The method according to any of aspects 109-123, wherein releasing the agent onto the eye includes releasing a medication onto the eye.
125. The method according to any of aspects 29, 48, 60, 71 or 84, wherein the release is a sustained release.

These and other examples, advantages, and features of the present lacrimal implants and methods will be set forth in part in following Detailed Description. This introduction is intended to provide an overview of subject matter of the present patent application. It is not intended to provide an exclusive or exhaustive explanation of the invention. The Detailed Description is included to provide further information about the present patent application.

BRIEF DESCRIPTION OF THE DRAWINGS

This patent document contains at least one drawing executed in color. Copies of this patent document with color drawings will be provided by the Office upon request and payment of the necessary fee.

In the drawings, like numerals can be used to describe similar components throughout the several views. Like numerals having different letter suffixes can be used to represent different instances of similar components. The drawings illustrate generally, by way of example, but not by way of limitation, various examples discussed in the present document.

DETAILED DESCRIPTION

In this patent document, lacrimal implants and related methods providing secure retention within the lacrimal punctum of an eye are described. The lacrimal implants can comprise a implant body configured for at least partial insertion through the lacrimal punctum and into a lacrimal canaliculus. The implant body can include a deformable retention structure that can be configured to substantially encapsulate an expandable retention element. In some examples, the expandable retention element can include a hydrogel material (i.e., a hydrogel retention element), which can be exposed to fluid such as via a fluid permeable retainer. As the hydrogel material absorbs or otherwise retains (e.g., adsorbs) such fluid (i.e., upon acceptance of fluid), its size increases and its shape changes such as to urge one or more portions of the retention structure outward, such as against a wall of the lacrimal canaliculus, thereby securely retaining the lacrimal implant within the punctum. In other examples, the expandable retention element can include a substantially non-fluid-absorbing material, which can be configured to expand or be expanded such as upon insertion through the lacrimal punctum and into the lacrimal canaliculus. In various examples, the lacrimal implant can further comprise a drug-releasing or other agent-releasing core housed by the implant body to provide sustained release of a therapeutic agent to the eye.

The present lacrimal implants can be securely retained in or near the eye, such as for successfully blocking the flow of tears or providing sustained delivery of a drug or other therapeutic agent to the eye. Substantially encapsulating the expandable retention element using portions of the implant body (e.g., a retention structure of the implant body) can inhibit the retention element from protruding out of the implant. Further, the expandable nature of the retention element allows for easier implantation, as much of the retention element expansion can be configured to occur after the implant is implanted as desired.

Figure 1:
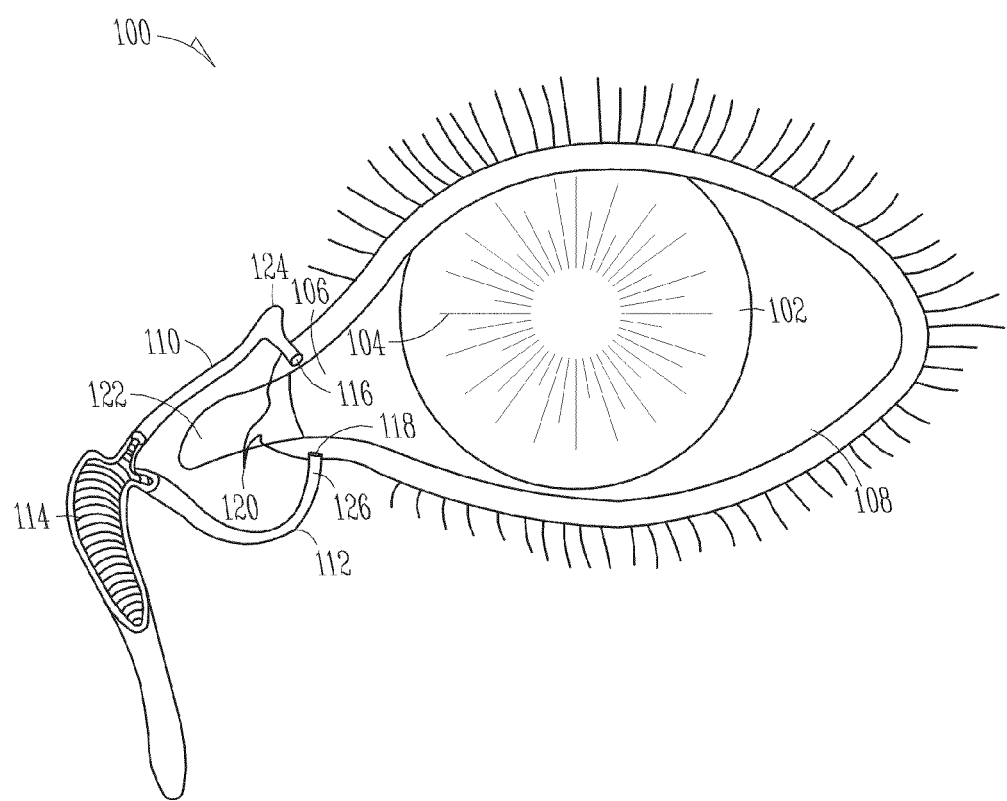
FIGS. 1-2 illustrate examples of schematic views of anatomical tissue structures associated with the eye, such tissue structures providing a suitable environment in which a lacrimal implant can be used.
Figure 2:
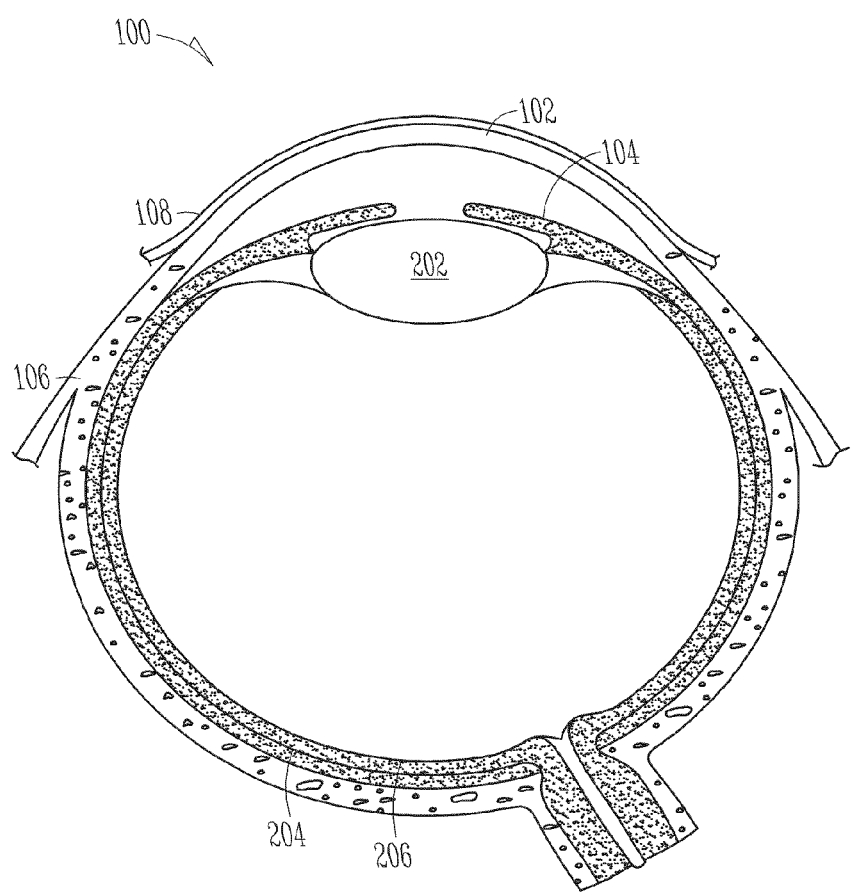

FIGS. 1-2 illustrate examples of schematic views of anatomical tissue structures associated with an eye 100. The anatomical tissue structures shown are suitable for treatment using the lacrimal implants and methods discussed herein, which can include a substantially encapsulated retention element. The eye 100 includes a cornea 102 and an iris 104 surrounded by a sclera 106. A transparent conjunctival layer 108 is disposed over the sclera 106. A lens 202 is located within the eye 100, while a retina 204 is located near the back of the eye 100. The retina 204 includes a fovea 206 which provides high visual acuity and color vision to the eye 100. In operation, the cornea 102 and lens 202 refract light to form an image on the fovea 206 and the retina 204.

Additional anatomical tissue structures associated with the eye 100 include the lacrimal system, which includes an upper lacrimal canaliculus 110 and a lower lacrimal canaliculus 112, and a naso-lacrimal duct or sac 114. The upper 110 and lower 112 canaliculus terminate in an upper lacrimal punctum 116 and a lower lacrimal punctum 118. The upper 116 and lower 118 punctum are slightly elevated at the medial end of a lid margin at the junction 120 of the ciliary and lacrimal portions near a medial canthus 122. The upper 116 and lower 118 punctum are generally round or slightly ovoid openings surrounded by a connective ring of tissue. Each of the punctas 116, 118 leads into a vertical portion 124, 126 of the respective canaliculus before turning horizontally to join one another at the entrance of the lacrimal sac 114. The canaliculae 110, 112 are generally tubular and lined by stratified squamous epithelium surrounded by elastic tissue which permits them to be dilated.

Figure 3A:
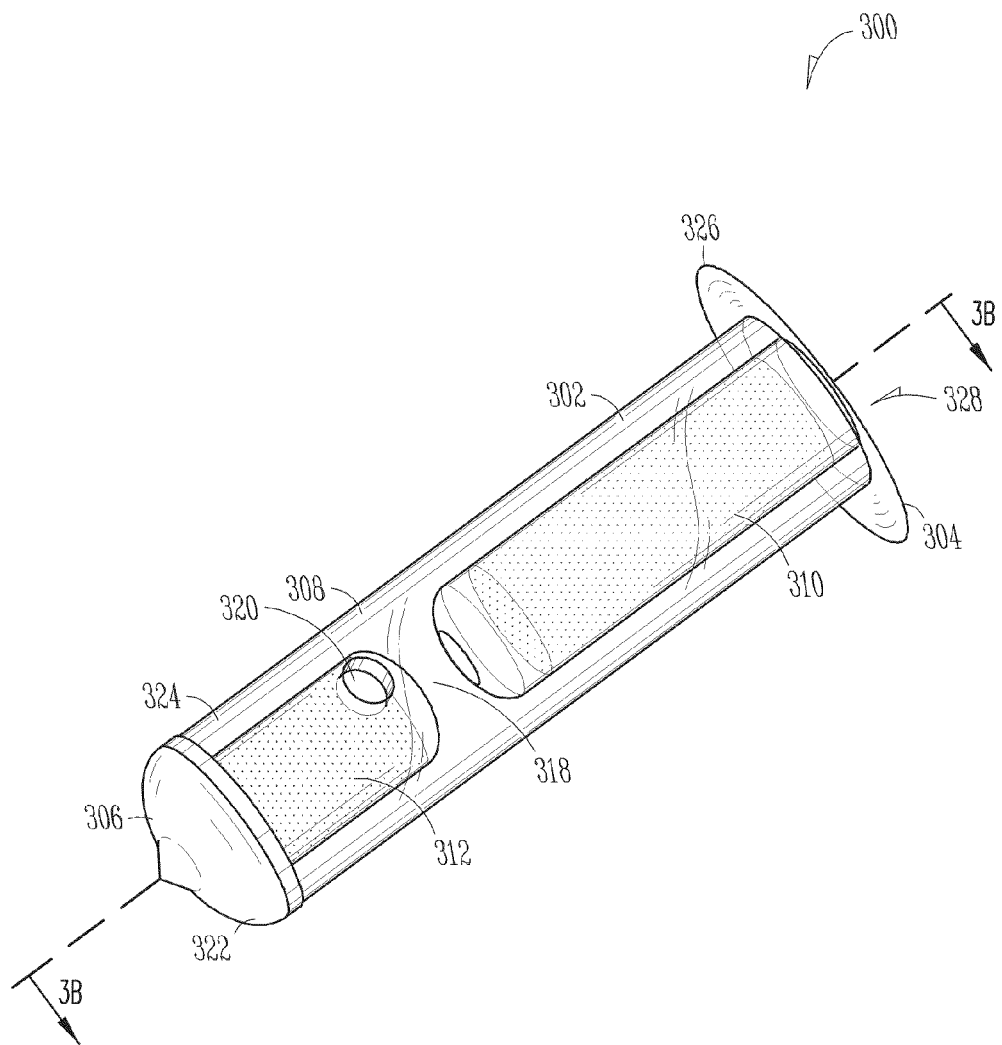
FIG. 3A illustrates an example of an isometric view of a lacrimal implant including an expandable retention element substantially encapsulated by a retention structure of a implant body.

FIG. 3A illustrates an example of a lacrimal implant 300 that is insertable into a lacrimal punctum. The insertion of the lacrimal implant 300 into the lacrimal punctum 116, 118 (FIG. 1) allows for one or more of inhibition or blockage of tear flow therethrough (e.g., to treat dry eyes) or the sustained delivery of a therapeutic agent to an eye (e.g., to treat one or more of infection, inflammation, glaucoma or other ocular diseases). In this example, the lacrimal implant 300 comprises a implant body 302 extending from a proximal end portion 304 to a distal end portion 306 and having a retention structure 308. In various examples, the implant body 302 can comprise an elastic material, such as silicone, polyurethane or other urethane-based material, or an acrylic of a non-biodegradable, partially biodegradable or biodegradable nature (i.e., erodeable within the body) allowing at least one portion of the retention structure to deform outward. In some examples, the biodegradable elastic materials include cross-linked polymers, such as poly (vinyl alcohol). In some examples, different portions of the implant body 302 are made of different materials. For instance, the implant body proximal end portion 304 can comprise a silicone/polyurethane co-polymer and the implant body distal end portion 306 can comprise a polyurethane hydrogel or other solid hydrogel. In certain examples, the implant body proximal end portion 304 can comprise silicone and the implant body distal end portion 306 can comprise a hydrophilic silicone mixture. Other co-polymers that can be used to form the implant body 302 include silicone/urethane, silicone/poly(ethylene glycol) (PEG), and silicone/2hydroxyethyl methacrylate (HEMA).

In certain examples, the implant body 302 can include a cylindrical-like structure having a first chamber 310 at or near the proximal end and a second chamber 312 at or near the distal end. A drug-releasing or other agent-releasing drug core 314 or other supply can be disposed in the first chamber 310, while a hydrogel or other expandable retention element 316 of a biodegradable or non-biodegradable nature can be disposed in the second chamber 312. In some examples, the biodegradable retention elements include salt- and cellulose-based mixtures. In some examples, the non-biodegradable retention elements include hydrogels, such as urethane-based hydrogels, or other synthetic polymers. As further discussed in commonly-owned Utkhede et al., U.S. patent application Ser. No. 12/231,986, titled "DRUG CORES FOR SUSTAINED RELEASE OF THERAPEUTIC AGENTS," which is herein incorporated by reference in its entirety, urethane-based polymer and copolymer materials allow for a variety of processing methods and bond well to one another. A implant body septum 318 can be positioned between the first chamber 310 and the second chamber 312 and can be used to inhibit or prevent communication of a material between the drug core 314 and the hydrogel retention element 316.

In various ways, the expandable, hydrogel retention element 316 can be substantially encapsulated, such as within a portion of the retention structure 308. In various examples, the retention structure 308 can include a fluid permeable retainer allowing fluid to be received into and absorbed or otherwise retained by the hydrogel retention element 316, such as upon its insertion into the punctum. The hydrogel retention element 316 can be configured to expand, such as to a size or shape that urges one or more outer surface portions of the retention structure 308 to contact a wall of the lacrimal canaliculus, thereby retaining or helping retain a least a portion of the implant within the punctum. In some examples, the fluid permeable retainer can include a fluid permeable aperture 320, such as disposed in a lateral wall of the retention structure 308. In some examples, the fluid permeable retainer can include a fluid permeable or hydrophilic cap member 322 or other membrane. In some examples, the fluid permeable retainer can include a fluid permeable or hydrophilic implant body portion 324. These examples of fluid permeable retainers 320, 322, and 324 can also inhibit the hydrogel retention element 316 from appreciably protruding out of the retention structure 308 during and upon expansion.

Figure 4:
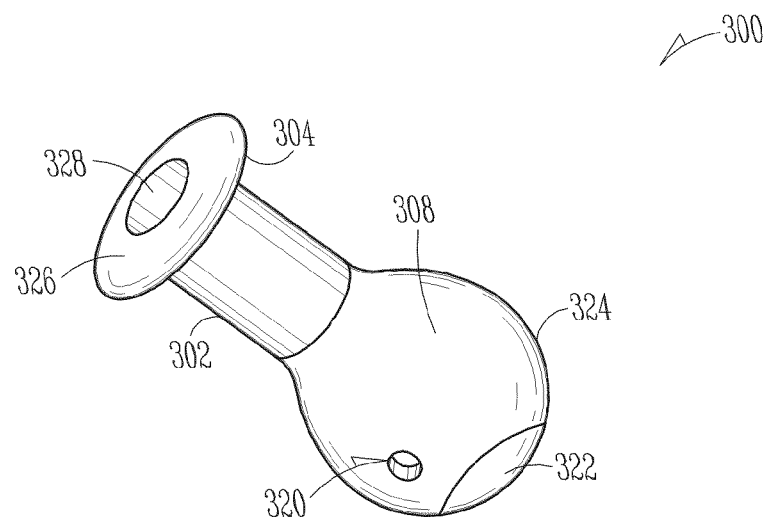
FIG. 4 illustrates an example of an isometric view of a lacrimal implant in an expanded state, the expanded state resulting, at least partially, from an increase in size of a substantially encapsulated retention element.
Figure 5:
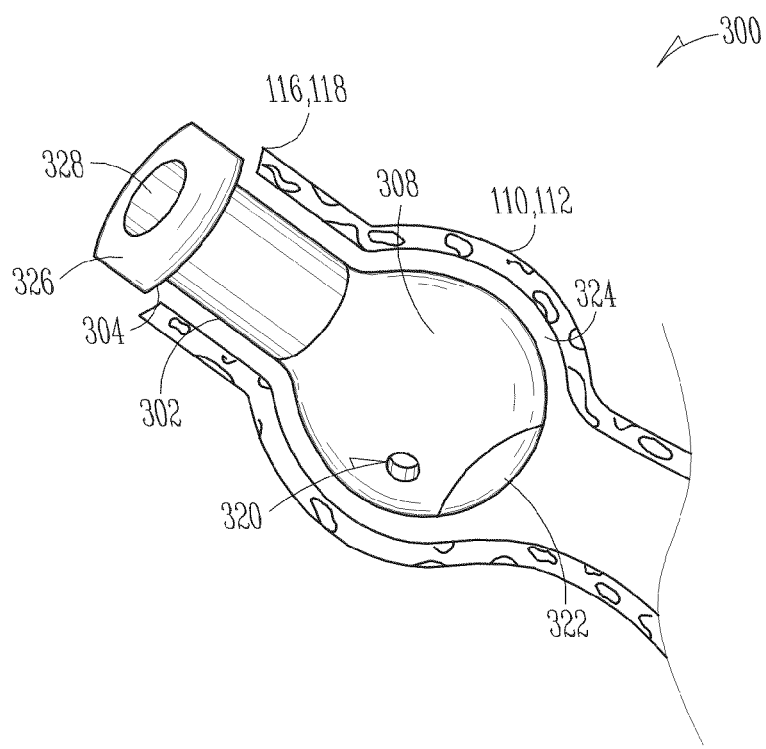
FIG. 5 illustrates an example of a schematic view of a lacrimal implant having an expanded state and retained within a lacrimal punctum.

The implant body 302 can include a feedback or other projection 326, such as extending laterally at least partially from or around (e.g., a removal loop) a proximal end portion 304 of the implant body 302. In some examples, the projection 326 can include a removal loop. In some examples, the projection 326 can be configured to seat against or near (e.g., via a ramped portion 360) the punctum opening 116, 118 (FIG. 1), such as for inhibiting or preventing the lacrimal implant 300 from passing completely within the canaliculus 110, 112 (FIG. 1), or for providing tactile or visual feedback information to an implanting user regarding the same. In some examples, a proximal end of the projection 326 can include a convex-shape such as for helping provide comfort to a patient when implanted. In some examples, the projection 326 can include a convex radius of about 0.8 millimeters. In some examples, the projection 326 is between about 0.7 millimeters to about 0.9 millimeters in diameter. In some examples, the projection 326 can include a non-convex shape of about 0.5 millimeters to about 1.5 millimeters in diameter, and 0.1 millimeters to about 0.75 millimeters in thickness. In some examples, the projection 326 has a wing-like shape, in which a column-like projection extends from opposite sides of the implant proximal end 304. In some examples, such as is shown in FIG. 5, the projection 326 includes a partially trimmed collar extending 360 degrees around the proximal end 304 from an outer implant body surface. In some examples, such as is shown in FIG. 4, the projection 326 includes a full collar extending 360 degrees around the proximal end 304 from an outer implant body surface. In an example, the projection 326 includes a cross-sectional shape similar to a flat disk (i.e., relatively flat top and bottom surfaces). A drug or other agent elution port 328 can extend though the projection 326, such as to provide sustained release of a drug core 314 agent onto an eye.

Figure 3B:
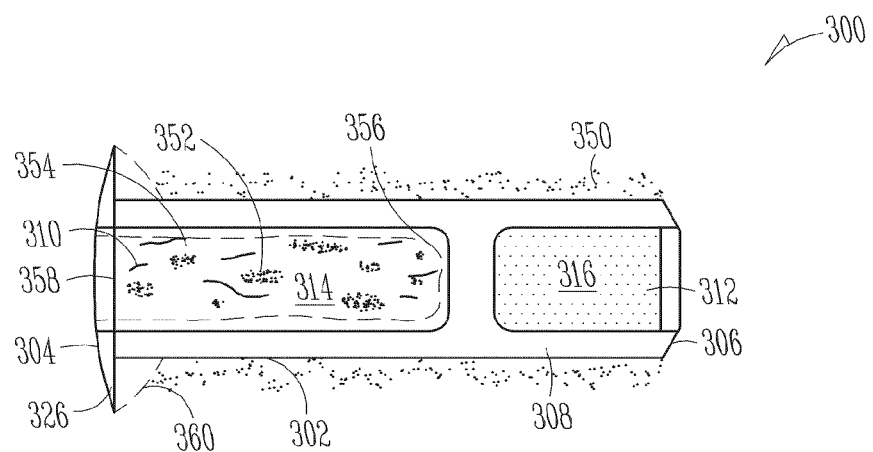
FIG. 3B illustrates an example of a cross-sectional view of a lacrimal implant taken along a line parallel to a longitudinal axis of the implant, such as along line 3B-3B.

In the example shown, the drug core 314 has a sheath body 356 disposed over at least a portion thereof such as to define at least one exposed surface 358 of the drug core. The exposed surface 358 can be located at or near the proximal end portion 304 of the implant body such as to contact a tear or a tear film fluid and release the therapeutic agent at one or more therapeutic levels over a sustained time period when the lacrimal implant 300 is inserted into the punctum. In an example, such as is shown in FIG. 3B, the exposed surface 358 of the drug core 314 can be flush or slightly below the proximal end of the projection 326 such that the drug core does not protrude outside of the implant body 302. In an example, as shown in FIG. 3D, the exposed surface 358 can be positioned above the proximal end of the projection 326 such that the drug core 314 at least partially protrudes outside of the implant body 302.

In some examples, by controlling geometry or a drug concentration gradient near the exposed surface 358 of the drug core 314, a predetermined drug or agent release rate can be achieved. For instance, the exposed surface 358 can be constructed with a specific geometry or other technique appropriate to control the release rate of the drug or other agent onto an eye 100, such as on an acute basis, or on a chronic basis between outpatient doctor visits, for example. Further discussion regarding effective release rates of one or more drugs or other agents from a drug supply 320 can be found in commonly-owned DeJuan et al., U.S. patent application Ser. No. 11/695,545, titled "NASOLACRIMAL DRAINAGE SYSTEM IMPLANTS FOR DRUG THERAPY," which is herein incorporated by reference in its entirety, including its description of obtaining particular release rate ranges.

FIG. 3B illustrates a cross-sectional view of an example of a lacrimal implant 300 taken along a line parallel to a longitudinal axis of the implant, such as along line 3B-3B of FIG. 3A. As shown in FIG. 3B, the lacrimal implant can include a implant body 302 having a retention structure 308 substantially encapsulating a hydrogel retention element 316 at or near a implant body distal end portion 306, and a drug-releasing or other agent-releasing core 314 disposed within the implant body, for example at or near a proximal end portion 304. In this example, the drug core 314 is disposed in a first implant body chamber 310 and the hydrogel retention element 316 is disposed in a second implant body chamber 312. As discussed above, the hydrogel retention element 316 can be configured to expand to a size or shape that retains or helps retain at least a portion of the implant 300 within the lacrimal punctum 116, 118 (FIG. 1). In some examples, a hydrogel retention element 350 can also be coated or otherwise provided on an outer surface portion of the implant body 302 providing another (e.g., secondary) mechanism for retaining or helping to retain at least a portion of the implant 300 at least partially within the lacrimal punctum.

The retention structure 308, which can be used to substantially encapsulate the hydrogel retention element 316, can be of varying sizes relative to a implant body 302 size. In some examples, the retention structure 308 is at least about one fifth the length of the implant body 302. In some examples, the retention structure 308 is at least about one fourth the length of the implant body 302. In some examples, the retention structure 308 is at least about one third the length of the implant body 302. In some examples, the retention structure 308 is at least about one half the length of the implant body 302. In some examples, the retention structure 308 is at least about three quarters the length of the implant body 302. In some examples, the retention structure 308 is about the full length of the implant body 302.

As shown in the example of FIG. 3B, the hydrogel retention element 316 can have a non-expanded, "dry" state, which aids insertion through the punctum 116, 118 and into the lacrimal canaliculus 110, 112 (FIG. 1). Once placed in the canaliculus, the hydrogel retention element 316 can absorb or otherwise retain canalicular or other fluid, such as via a fluid permeable retainer 320, 322, 324 (FIG. 3A) to form an expanded structure. In some examples, the hydrogel retention element 316 can include a material that is non-biodegradable. In some examples, the hydrogel retention element 316 can include a material that is biodegradable. Other options for the hydrogel retention element 316 can also be used. For instance, the hydrogel retention element 316 can be molded with the retention structure 308 in a single piece, or can be formed separately as one piece and subsequently coupled to the retention structure 308.

In some examples, the drug core 314 disposed at or near the proximal end portion 304 of the implant body 302 can include a plurality of therapeutic agent inclusions 352, which can be distributed in a matrix 354. In some examples, the inclusions 352 comprise a concentrated form of the therapeutic agent (e.g., a crystalline agent form). In some examples, the matrix 354 can comprise a silicone matrix or the like, and the distribution of inclusions 352 within the matrix can be non-homogeneous. In some examples, the agent inclusions 352 include droplets of an oil, such as latanoprost oil. In still other examples, the agent inclusions 352 comprise solid particles, such as Bimatoprost particles in crystalline form. In some examples, the drug core 314 comprises a urethane-based (e.g., polyurethane) polymer or copolymer comprising therapeutic agent inclusions deliverable into the eye or surrounding tissues, such as is discussed in commonly-owned Utkhede et al., U.S. patent application Ser. No. 12/231,986, titled "DRUG CORES FOR SUSTAINED RELEASE OF THERAPEUTIC AGENTS," which is herein incorporated by reference in its entirety. The inclusions can be of many sizes and shapes. For instance, the inclusions can be microparticles having dimensions on the order of about 1 micrometers to about 100 micrometers.

In the example shown, the drug core 314 has a sheath body 356 disposed over at least a portion thereof such as to define at least one exposed surface 358 of the drug core. The exposed surface 358 can be located at or near the proximal end portion 304 of the implant body such as to contact a tear or a tear film fluid and release the therapeutic agent at one or more therapeutic levels over a sustained time period when the lacrimal implant 300 is inserted into the punctum.

Figure 3C:
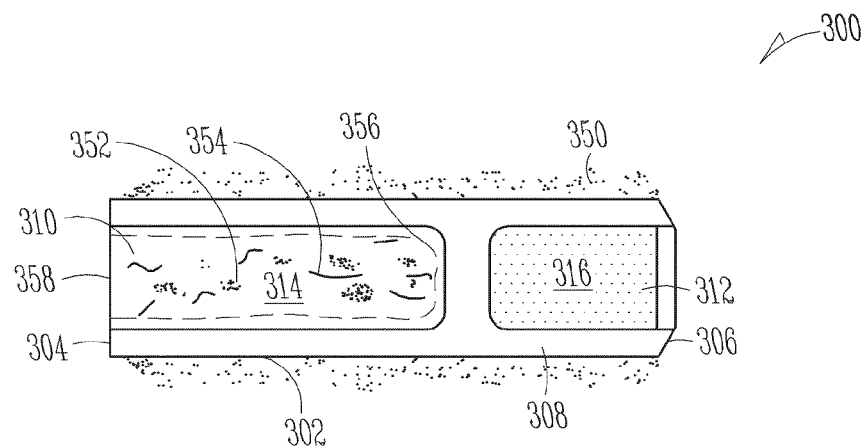
FIG. 3C illustrates an example of a cross-sectional view of another lacrimal implant taken along a line parallel to a longitudinal axis of the implant.
Figure 3D:
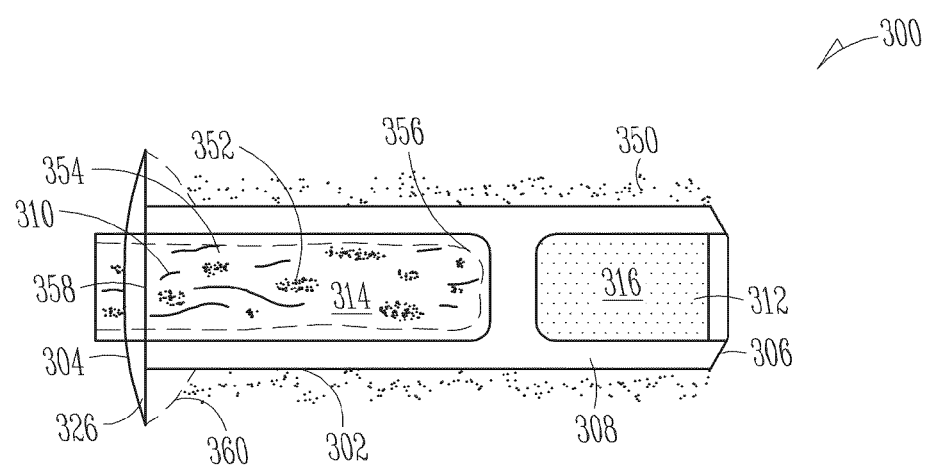
FIG. 3D illustrates an example of a cross-sectional view of another lacrimal implant taken along a line parallel to a longitudinal axis of the implant.

FIG. 3C illustrates a cross-sectional view of an example of a lacrimal implant 300 taken along a line parallel to a longitudinal axis of the implant. As shown in FIG. 3C, the lacrimal implant includes a implant body 302 without a feedback or other projection 326 (FIG. 3A). In this way, the implant 300 can be completely inserted inside the lacrimal punctum 116, 118 (FIG. 1). In some examples, the first chamber 310 can include dimensions of about 0.013 inches×about 0.045 inches. In some examples, the second chamber 312 can include dimensions of about 0.013 inches×about 0.020 inches.

FIG. 4 illustrates an isometric view of a lacrimal implant 300 in an expanded, hydrated state resulting from an increase in size of a substantially encapsulated hydrogel retention element 316 (FIG. 3A). Due to the expansion of the substantially encapsulated hydrogel retention element 316, one or more outer surface portions of the implant body's retention structure 308 can be urged outward, such as to a size and shape of a canaliculus wall to securely retain a desired position of the implant 300, as shown in FIG. 5. Optionally, a feedback or other projection 326 extending at least partially from or around a proximal end portion of the implant body 302 can be seated against a punctum 116, 118 such as to inhibit or prevent over-insertion of the implant into the canaliculus, as further shown in FIG. 5.

As previously discussed, in some examples, the retention structure 308 can include a fluid permeable retainer allowing fluid to be received into and absorbed or otherwise retained by the hydrogel retention element 316, such as upon insertion through the lacrimal punctum 116, 118 (FIG. 1) and into a lacrimal canaliculus 110, 112 (FIG. 1). In the example shown, but as may vary, the fluid permeable retainer includes at least one fluid permeable aperture 320, such as disposed in a lateral wall of the retention structure 308. In some examples, the fluid permeable retainer can include a fluid permeable or hydrophilic cap member 322 (FIG. 3A). In some examples, the fluid permeable retainer can include a fluid permeable or hydrophilic implant body portion 324 (FIG. 3A). Besides allowing fluid into the retention structure 308, each of these fluid permeable retainers 320, 322, and 324 can inhibit or prevent the hydrogel retention element 316 from protruding out of the retention structure during and upon expansion.

By configuring a composition of the hydrogel retention element 316, various expansion characteristics can be achieved. In some examples, the hydrogel retention element composition allows for an expansion capacity of up to 1 time its "dry" volume. In some examples, the hydrogel retention element composition allows for an expansion capacity of up to 10 times its "dry" volume. In some examples, the hydrogel retention element composition allows for an expansion capacity of up to 100 times its "dry" volume.

Figure 6:
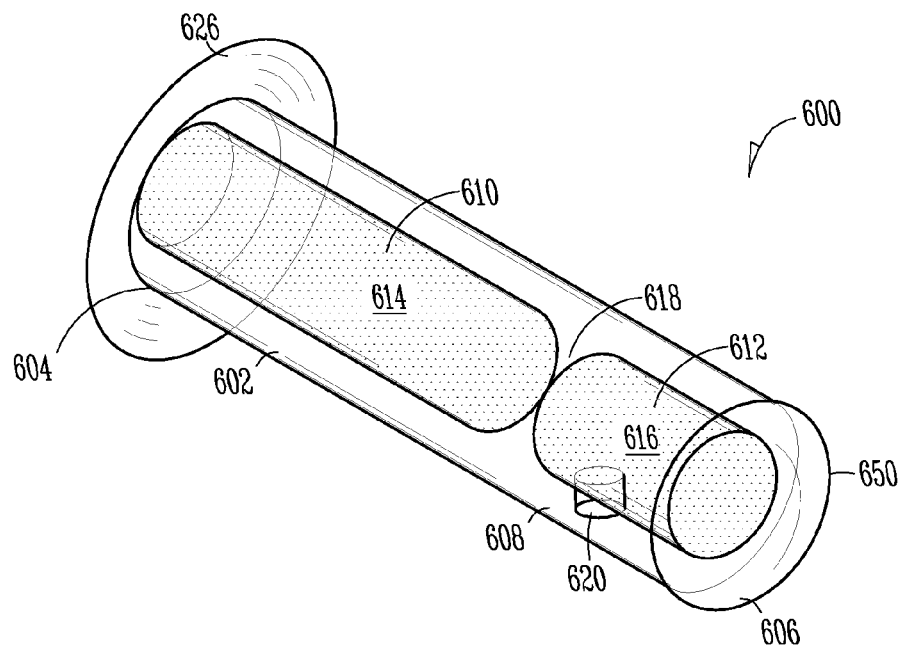
FIG. 6 illustrates an example of an isometric view of another lacrimal implant including an expandable retention element substantially encapsulated by a retention structure of a implant body.

FIG. 6 illustrates another example of a lacrimal implant 600 that is at least partially insertable through a punctum and into a lacrimal canaliculus. This example of the lacrimal implant 600 comprises a implant body 602 extending from a proximal end portion 604 to a distal end portion 606, and having a deformable retention structure 608. In various examples, the implant body 602 can comprise an elastic material, such as silicone or polyurethane, of a non-biodegradable or biodegradable nature. In some examples, different portions of the implant body 602 are made of different materials.

In the example shown, the implant body 602 includes a cylindrical-like structure having a first chamber 610 at or near the proximal end and a second chamber 612 at or near the distal end. A drug core 614 can be disposed in the first chamber 610, while an expandable, hydrogel retention element 616 can be disposed in the second chamber 612. A implant body septum 618 positioned between the first chamber 610 and the second chamber 612 can be used to inhibit or prevent fluid or other material communication between the drug core 614 and the hydrogel retention element 616. In some examples, the implant body 602 can include a feedback or other projection 626 extending at least partially from or around the proximal end portion 604 of the implant body 602, or a non-permeable, non-hydrophilic cap member 650 coupled to the distal end portion 606 of the implant body.

In various ways, the expandable, hydrogel retention element 616 can be substantially encapsulated within at least a portion of the retention structure 608. In various examples, the retention structure 608 can include a fluid permeable retainer that can include at least one fluid permeable aperture 620, which allows fluid to be received into and absorbed or otherwise retained by the hydrogel retention element 616, such as upon insertion through the lacrimal punctum 116, 118 (FIG. 1) and into a lacrimal canaliculus 110, 112 (FIG. 1). The aperture 620 can include a size or shape that is large enough to accept fluid into the retention structure 608, but small enough to inhibit the hydrogel retention element 616 from appreciably protruding out the retention structure during and upon expansion. In some examples, the aperture has a diametrical size of about 0.30 millimeters or less, such as about 0.30 millimeters or less, or about 0.15 millimeters or less. In some examples, the aperture has a diametrical size of about 0.12 millimeters or less. In various examples, the aperture is sized and shaped to inhibit the escape of the hydrogel retention element 616, such that expulsion thereof is limited to less than 10%, less than 5%, or less than 1% of an expanded hydrogel volume. In a further example, a low molecular weight membrane or other barrier is disposed over at least a portion of the aperture 620, such as to further inhibit the escape of the hydrogel retention element 616. In various examples, the low molecular weight membrane includes a molecular weight less than the retention element. In some such examples, the low molecular weight membrane includes a molecular weight less than 10,000 daltons.

Figure 7:
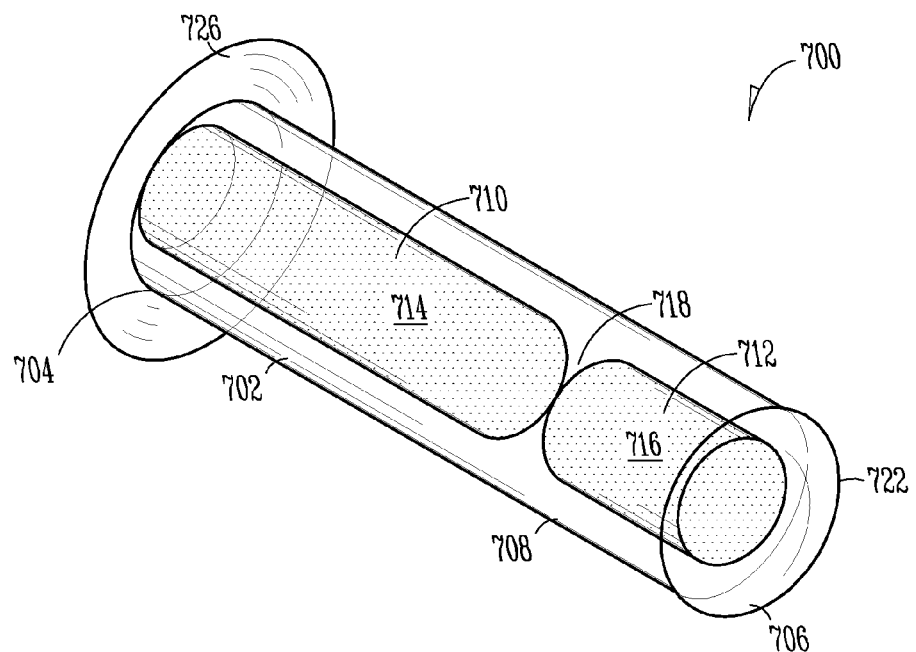
FIG. 7 illustrates an example of an isometric view of another lacrimal implant including an expandable retention element substantially encapsulated by a retention structure of a implant body.

FIG. 7 illustrates another example of a lacrimal implant 700 that is at least partially insertable through a punctum and into a lacrimal canaliculus. The lacrimal implant 700 can comprise a implant body 702 extending from a proximal end portion 704 to a distal end portion 706, and having a deformable retention structure 708. In various examples, the implant body 702 can comprise an elastic material, such as silicone or polyurethane, of a non-biodegradable or biodegradable nature. In some examples, different portions of the implant body 702 are made of different materials.

In the example shown, the implant body 702 includes a cylindrical-like structure having a first chamber 710 at or near the proximal end and a second chamber 712 at or near the distal end. A drug core 714 can be disposed in the first chamber 710, while an expandable, hydrogel or other retention element 716 can be disposed in the second chamber 712. A implant body septum 718 positioned between the first chamber 710 and the second chamber 712 can be used to inhibit or prevent fluid or other material communication between the drug core 714 and the hydrogel retention element 716. In some examples, the implant body 702 can include a feedback or other projection 726 extending at least partially from or around the proximal end portion 704 of the implant body 702 such as for providing a user with visual or tactile feedback, such as is described above.

In various ways, the expandable, hydrogel retention element 716 can be substantially encapsulated within a portion of the retention structure 708. In various examples, the retention structure 708 can include a fluid permeable retainer such as a fluid permeable or hydrophilic cap member 722, which allows fluid to be received into and absorbed or otherwise retained (e.g., adsorption) by the hydrogel retention element 616, such as upon insertion through the lacrimal punctum 116, 118 (FIG. 1) and into a lacrimal canaliculus 110, 112 (FIG. 1). The cap member 722 can be configured to allow fluid into the retention structure 708, but to inhibit or prevent the hydrogel retention element 716 from appreciably protruding out of the retention structure during and upon expansion. In some examples, the cap member 722 can include a tapered distal tip portion such as to facilitate atraumatic insertion of the implant 700 through the lacrimal punctum and into the lacrimal canaliculus. In some examples, the cap member 722 can include at least 50 wt. % silicone in combination with at least one of a contact lens material (e.g., a contact lens material including at least one of a hydrogel, or a HEMA copolymer, PMMA copolymer; or VSO 75), sodium chloride, polyethylene oxide, polyethylene glycol, polyvinyl pyrilidone (e.g., poly(1-(2-oxo-1-pyrrolidinyl)ethylene), or polyvinyl alcohol. For instance, the cap member 722 can include 80% silicone and 20% contact lens material, a form of which is available from Vista Optics. In various examples, the contact lens material can include non-ionic polymers having less than 50% water (e.g., tefilcon (38%), tetrafilcon A (43%), crofilcon (38%), helfilcon (45%), mafilcon (33%), or polymacon (38%)), non-ionic polymers having greater than 50% water (e.g., lidofilcon B (79%), surfilcon A (74%), lidofilcon A (70%), netrafilcon A (65%), hefilcon C (57%), alfafilcon A (66%), omafilcon A (59%), vasurfilcon A (74%), hioxifilcon A (59%), nelfilcon A (69%), hilafilcon A (70%), or hilafilcon B (59%)), ionic polymers having less than 50% water (e.g., bufilcon A (45%), deltafilcon A (43%), or phemfilcon (38%)), or ionic polymers having greater than 50% water (e.g., bufilcon A (55%), perfilcon A (71%), etafilcon A (58%), focofilcon A (55%), ocufilcon B (53%), ocufilcon C (55%), ocufilcon D (55%), ocufilcon E (65%), ocufilcon F (60%), phemfilcon A (55%), methafilcon A (55%), methafilcon B (55%), or vilfilcon A (55%)).

Examples of some additional options for the cap member 722 can be as follows. In some examples, the cap member 722 is disposed at a distal end portion of the retention structure 708. In some examples, the cap member 722 is sized and shaped to cover only the distal end of the retention structure 708. In some examples, the cap member 722 is flush with the distal end of the retention structure 708. In some examples, the cap member 722 is recessed within an inner wall of the retention structure 708.

Figure 8:
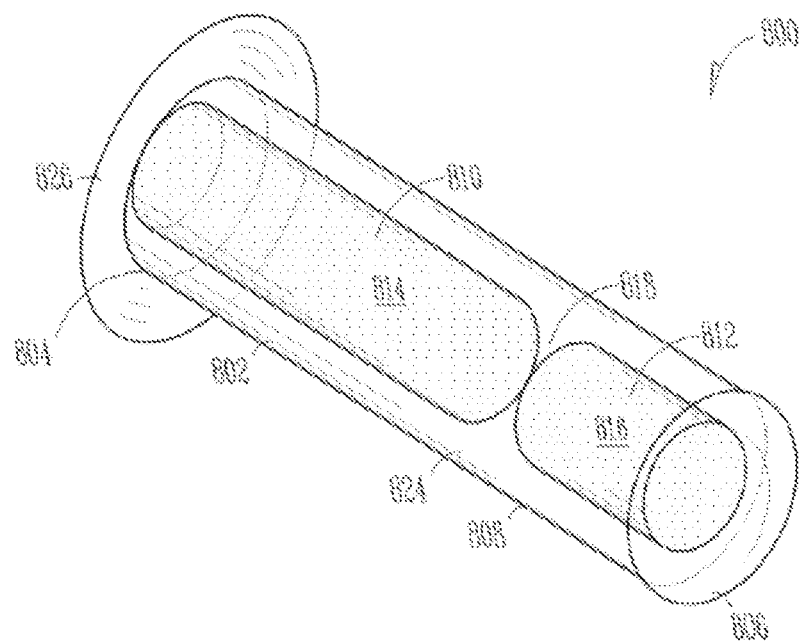
FIG. 8 illustrates an example of an isometric view of another lacrimal implant including an expandable retention element substantially encapsulated by a retention structure of a implant body.

FIG. 8 illustrates another example of a lacrimal implant 800 that is at least partially insertable through a punctum and into a lacrimal canaliculus. The lacrimal implant 800 can comprise a implant body 802 extending from a proximal end portion 804 to a distal end portion 806, and having a retention structure 808. In various examples, the implant body 802 can comprise an elastic material, such as silicone or polyurethane, of a non-biodegradable or biodegradable nature. In some examples, different portions of the implant body 802 are made of different materials.

In the example shown, the implant body 802 includes a cylindrical-like structure having a first chamber 810 at or near the proximal end and a second chamber 812 at or near the distal end. A drug core 814 can be disposed in the first chamber 810, while an expandable, hydrogel retention element 816 can be disposed in the second chamber 812. A implant body septum 818 positioned between the first chamber 810 and the second chamber 812 can be used to inhibit or prevent fluid or other material communication between the drug core 814 and the hydrogel retention element 816. The implant body 802 can include a feedback or other projection 826 extending at least partially from or around the proximal end portion 804 of the implant body 802, such as for providing visual or tactile feedback to a user during implantation.

In various ways, the expandable, hydrogel retention element 816 can be substantially encapsulated within a portion of the retention structure 808. In various examples, the retention structure 808 can include a fluid permeable retainer in the form of a fluid permeable or hydrophilic implant body portion 824, which allows fluid to be received into and absorbed or otherwise retained by the hydrogel retention element 816, such as upon insertion through the lacrimal punctum 116, 118 (FIG. 1) and into a lacrimal canaliculus 110, 112 (FIG. 1). In some examples, the fluid permeable or hydrophilic body portion 824 can include at least 50 wt. % silicone in combination with at least one of a contact lens material (e.g., a contact lens material including at least one of hydrogel, a HEMA copolymer, or a PMMA copolymer), sodium chloride, polyethylene oxide, polyethylene glycol, polyvinyl pyrilidone, or polyvinyl alcohol. In some examples, the fluid permeable or hydrophilic body portion 824 can comprise about 5% to about 50% of the implant body 802 lateral surface area within the punctum. In some examples, the fluid permeable or hydrophilic body portion 824 can comprise greater than 50% of the implant body 802 lateral surface area within the punctum, such as about 100% of the implanted implant body surface area.

Figure 9:
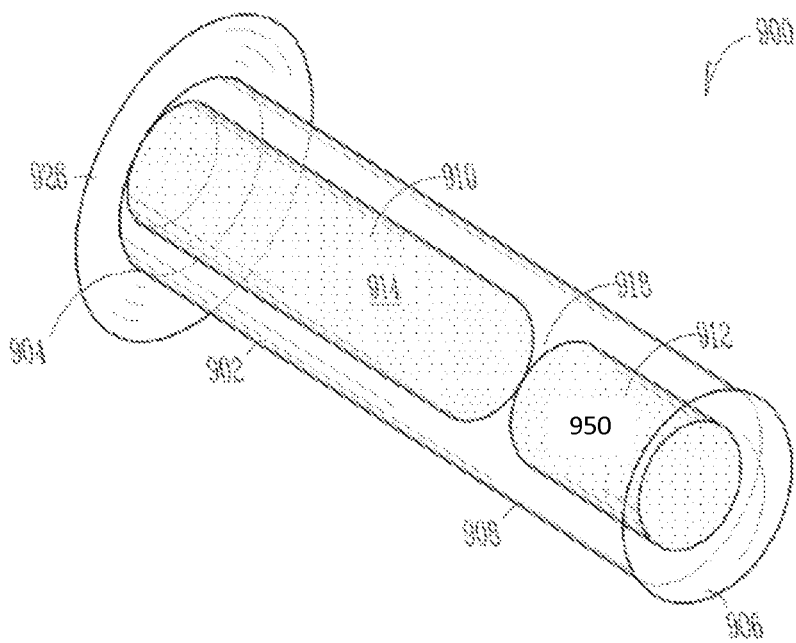
FIG. 9 illustrates an example of an isometric view of yet another lacrimal implant including an expandable retention element substantially encapsulated by a retention structure of a implant body.

FIG. 9 illustrates another example of a lacrimal implant 900 that is at least partially insertable through a punctum and into a lacrimal canaliculus. The lacrimal implant 900 can comprise a implant body 902 extending from a proximal end portion 904 to a distal end portion 906, and having a deformable retention structure 908. In various examples, the implant body 902 can comprise an elastic material, such as silicone or polyurethane, of a non-biodegradable or biodegradable nature. In some examples, different portions of the implant body 902 are made of different materials.

In the example shown, the implant body 902 includes a cylindrical like structure having a first chamber 910 at or near the proximal end and a second chamber 912 at or near the distal end. A drug core 914 can be disposed in the first chamber 910, while an expandable, substantially non-fluid-absorbing retention element 950 can be disposed in the second chamber 912. An implant body septum 918 positioned between the first chamber 910 and the second chamber 912 can be used to inhibit or prevent fluid or other material communication between the drug core 914 and the non-fluid-absorbing retention element 950. In some examples, the implant body 902 can include a feedback or other projection 926 extending at least partially from or around the proximal end portion 904 of the implant body 902, such as for providing visual or tactile feedback to an implanting user.

In various ways, the expandable, non-fluid-absorbing retention element 916 can be fully encapsulated within a portion of the retention structure 908. In contrast to a hydrogel retention element, the non-fluid-absorbing retention element 916 need not use a fluid permeable retainer to allow for the receipt of fluid. Rather, the non-fluid-absorbing retention element 916 can be configured such that actuation to an expanded size or shape is otherwise achievable, such as via a specified temperature (e.g., a temperature that is present within the lacrimal punctum or lacrimal canaliculus, such as upon insertion therein). In some examples, the non-fluid-absorbing retention element 916 can include a shape-memory thermoplastic. In some such examples, the non-fluid-absorbing retention element 916 is urethane-based. In some examples, the non-fluid-absorbing retention element 916 can include an oxidation-producing system that is configured to generate and release one or a plurality of oxides, which are collected in the encapsulated provided by the retention structure 908.

Figure 10:
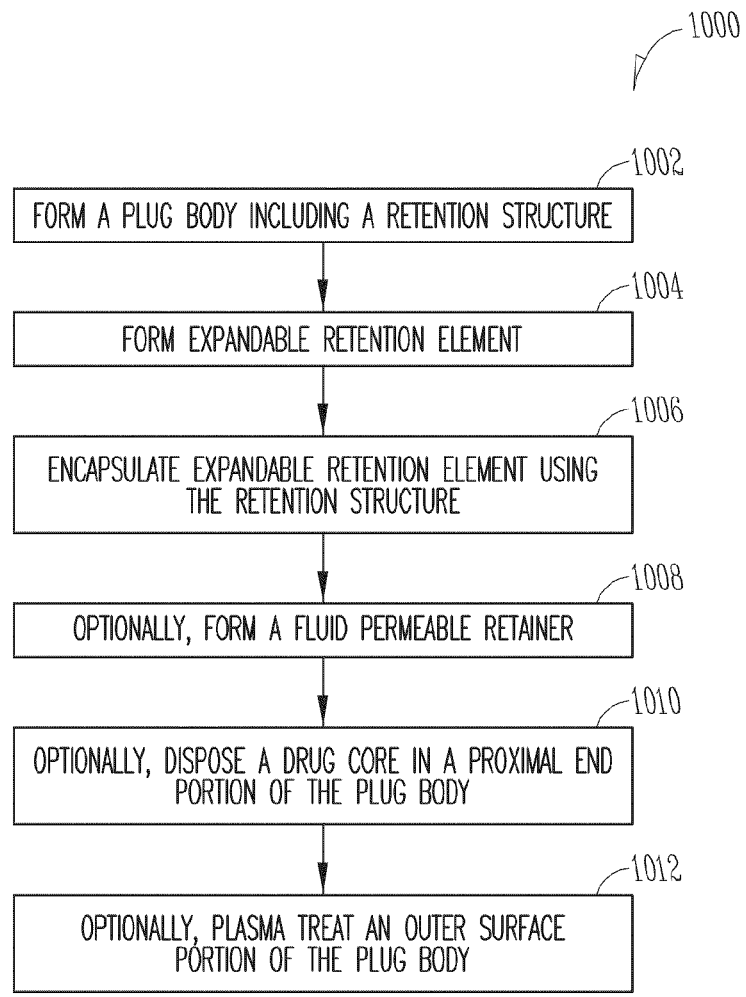
FIG. 10 illustrates an example of a method of manufacturing a lacrimal implant including an expandable retention element substantially encapsulated by a retention structure of a implant body.
Figure 11:
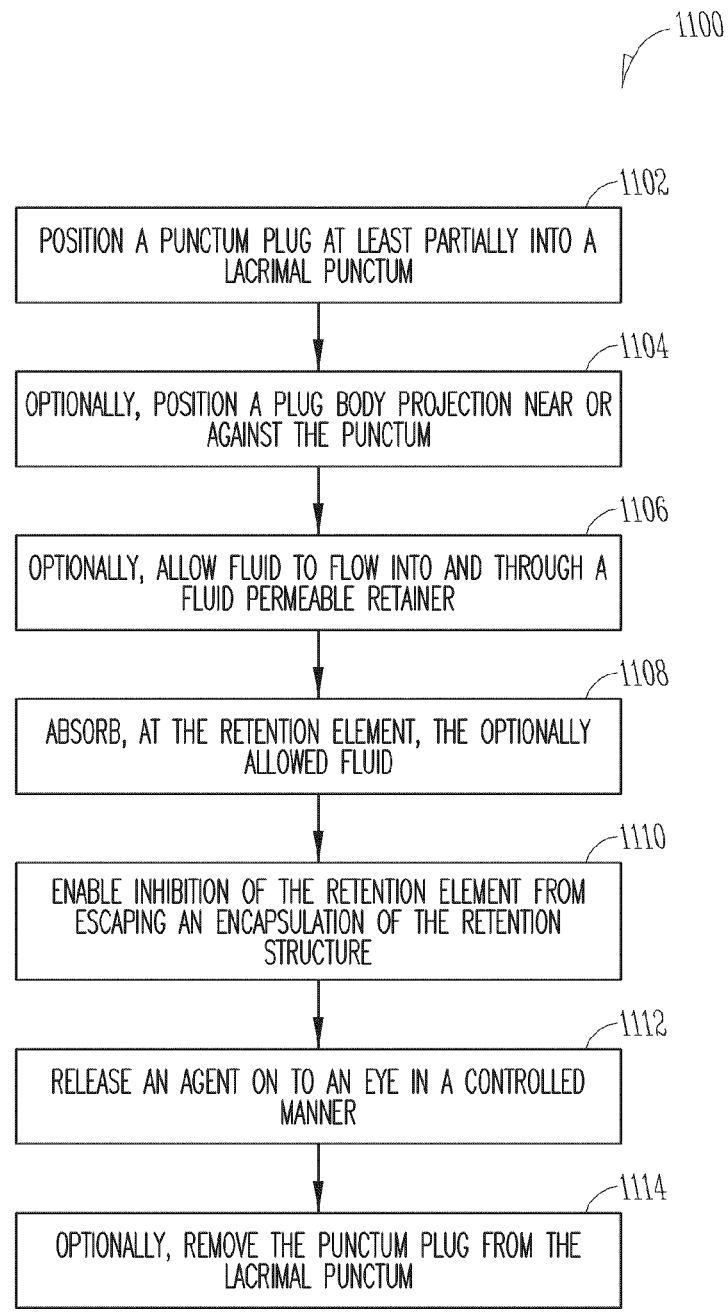
FIG. 11 illustrates an example of a method of treating an eye using a lacrimal implant.

FIG. 10 is a block diagram illustrating an example of a method 1000 of manufacturing a lacrimal implant configured to be at least partially insertable into a lacrimal punctum. At 1002, a implant body extending from a proximal end portion to a distal end portion and including a retention structure is formed. In some examples, the proximal end portion of the implant body is formed to further include a implant body projection, such as a projection configured to providing visual or tactile feedback or configured to seat against a portion of the punctum and having a proximal convex-shape for patient comfort. In some examples, an intermediate portion of the implant body is formed to include a septum separating a first implant body portion and a second implant body portion. In some examples, the implant body is formed by concurrently or consecutively injection molding the first implant body portion and the second implant body. In some such examples, the first implant body portion is formed by injection molding a non-permeable, non-hydrophilic material, and the second implant body portion is formed by injection molding a fluid permeable or hydrophilic material.

At 1004, an expandable retention element is formed. In some examples, the expandable retention element can include a hydrogel-based material mixture that is configured to expand to a size or shape that, when substantially encapsulated by the retention structure of the implant body, securely retains the implant at least partially within the lacrimal punctum. In some such examples, the hydrogel material is configured to expand against a wall of a lacrimal punctum or canaliculus within a time period of about 1 minute to about 60 minutes, such as between about 20 minutes to about 30 minutes. An expansion amount (e.g., swelling) of the hydrogel material can be controlled by varying the ratio of hydrogel to the ratio of polymer (e.g., polyurethane or silicone) in the material mixture. In other examples, the expandable retention element can include a non-fluid-absorbing material, such as a shape-memory thermoplastic or an oxidation generating system, which can be temperature activated to increase in size and shape.

At 1006, the expandable retention element can be substantially encapsulated using the retention structure of the implant body. As a result, when the retention element expands in size and shape, such as when it swells with retained fluid, at least one outer surface portion of the retention structure is urged against a wall of the lacrimal canaliculus. In some examples, substantial encapsulation of the retention element can include disposing the retention element in a chamber of the retention structure.

Optionally, at 1008, a fluid permeable retainer between the retention element and the lacrimal canaliculus is formed. The fluid permeable retainer allows an absorbing or other fluid-retaining retention element, such as hydrogel, to receive and take-in fluid while in its substantially encapsulated position. In some examples, formation of the fluid permeable retainer is effectuated by forming a fluid permeable aperture or other fluid passage in a wall of the implant body. In various examples, the aperture has a size and shape inhibiting the escape of the retention element from the retention structure. In some examples, formation of the fluid permeable retainer is effectuated by forming a fluid permeable or hydrophilic cap member and coupling the cap to the distal end portion of the implant body. In some examples, formation of the fluid permeable retainer is effectuated by forming an integral fluid permeable or hydrophilic implant body portion. Among other material mixtures, the cap member and the integral fluid receiving portion of the implant body can include a mixture or other combination of at least about 50 wt. % silicone and at least one of a contact lens material, sodium chloride, polyethylene oxide, polyethylene glycol, polyvinyl pyrilidone, or polyvinyl alcohol.

Optionally, at 1010, a drug core is disposed in the proximal end portion of the implant body, such that a sustained release of an agent can be delivered to an adjacent eye. In some examples, the drug core is disposed in a implant body chamber proximal of the retention element and separated therefrom via the implant body septum. Optionally, at 1012, an outer surface portion of the implant body is plasma treated to allow for a fluid swellable material coating to adhere thereto. In some examples, the fluid swellable material coating can include a hydrogel material, which, when contacted with fluid, expands such as to provide a secondary mechanism for retaining the implant body at least partially within the lacrimal canaliculus. In some examples, the fluid swellable material is coated onto a non-plasma treated outer surface of a silicone/polyurethane implant body. Among other techniques, the fluid swellable material can be coated on the implant body outer surface via dip coating or spray coating.

Optionally, the outer surface portion of the implant body can be formed, or surface treated to be, generally smooth to inhibit bacteria from attaching to the lacrimal implant and incubating. The generally smooth outer surface can also prevent damage to the inner lining of the receiving anatomical tissue, such as a lacrimal punctum or the associated lacrimal canaliculus, during implantation. As further discussed in commonly-owned Rapacki et al., U.S. patent application Ser.

No. 12/283,002, titled "SURFACE TREATED IMPLANTABLE ARTICLES AND RELATED METHODS," which is herein incorporated by reference in its entirety, the outer surface of the implant body, for instance, can be improved via a polishing procedure using dichloride methane or other suitable media in conjunction with a tumbling process.

An example method of treating a subject (e.g., human being) having an eye disorder can include at least one of the following. The lacrimal implant can be at least partially inserted into the lacrimal punctum such that a retention element substantially encapsulated by a implant body retention structure and accessible via a fluid permeable retainer is disposed within the canaliculus. In some examples, the lacrimal implant is positioned into the lacrimal punctum using an insertion tool, such as is discussed in commonly owned DeJuan et al., International Patent Application No. PCT/US2007/065789, titled "NASOLACRIMAL DRAINAGE SYSTEM IMPLANTS FOR DRUG THERAPY," which is herein incorporated by reference in its entirety including its description of lacrimal implant positioning. Optionally, a feedback or other projection extending from a proximal end portion of the implant body can be seated against a portion of the punctum, such as for providing visual or tactile user feedback for ensuring the retention element is properly positioned.

Fluid can optionally be allowed into and through the communication means and received by the retention element. The fluid optionally received by the retention element can be absorbed or otherwise retained, causing the retention element to expand from a first size and shape insertable within the lacrimal punctum to a second size and shape that retains or helps retain at least a portion of the implant therein. In some examples, expansion of the retention element urges an outer surface portion of the substantially encapsulating retention structure to contact a wall of the lacrimal canaliculus or the lacrimal lake. In some examples, expansion of the retention element results from fluid absorption or other fluid retention during a time period of about 1 minute to about 60 minutes.

The retention element can inhibited from escaping the substantial encapsulation of the retention structure, in part, due to the structural support provided by the fluid permeable retainer. In some examples, escape of the retention element is inhibited through the use of a fluid permeable retainer in the form of a fluid permeable aperture having a diametrical size of about 0.30 mm or less. In some examples, escape inhibition of the retention element is effectuated through the use of a fluid permeable retainer in the form of a fluid permeable or hydrophilic cap member coupled to a distal end portion of the implant body. In some examples, escape inhibition of the of the retention element is effectuated through the use of a fluid permeable retainer in the form of an integral fluid permeable or hydrophilic implant body portion.

Optionally, a drug core agent, such as a drug or other therapeutic agent, can be gradually released, such as over a time period of at least one week, at least one month, or at least three months, to the eye from a drug elution port at the proximal end portion of the implant body. In some examples, the agent released is a medication to treat glaucoma disease, such as ocular hypertension or primary open angle glaucoma. Optionally, after a time period of 1 month, 2 months, 3 months or more, the implant can be removed from the lacrimal canaliculus such as by grabbing onto the implant body projection and pulling, or a new drug core is inserted into the implant either in situ or after removal. In some examples, upon removal of the first implant, a second implant having the same, lower or higher agent dosage within the drug core is inserted into the lacrimal punctum. In some examples, the removal and replacement of the lacrimal implants is repeated until the subject no longer requires treatment, such as after two, three, four or five iterations.

Sheath Body Examples:

In various ways, the sheath body can comprise appropriate shapes and materials to control migration of the agent from the drug core. As discussed, in some examples, the sheath body houses the core and can fit snugly against the core. The sheath body can be made from a material that is substantially impermeable to the agent so that the rate of migration of the agent is largely controlled by the exposed surface area of the drug core that is not covered by the sheath body. In many examples, migration of the agent through the sheath body can be about one tenth of the migration of the agent through the exposed surface of the drug core, or less. Suitable sheath body materials include, among others, polyimide, polyethylene terephthalate (PET). The sheath body can have a thickness, as defined from the sheath surface adjacent the core to an opposing sheath surface away from the core, of about 0.00025 inches' to about 0.0015 inches'. The total diameter of the sheath that extends across the drug core ranges from about 0.2 millimeters to about 1.2 millimeters. The drug core can be formed by dip coating the core in the sheath body. In some examples, the sheath body can comprise a tube into which the core is introduced. The sheath body can also be dip coated around the core, for example dip coated around a pre-formed core.

The sheath body can be provided with one or more additional features such as to facilitate clinical use of the lacrimal implants discussed herein. For example, the sheath can receive a drug core that is exchangeable in situ, while the retention structure and sheath body remain implanted in the patient, or after its removal. In some examples, the sheath body can be provided with one or more external protrusions that apply force to the sheath body when squeezed, which cause the core to be ejected from the sheath body. A replacement drug core can then be positioned in the sheath body. In some examples, the sheath body or retention structure can have a distinguishing feature, for example a distinguishing color, to show proper placement within the canaliculus.

Therapeutic Agent Examples:

A therapeutic agent (or simply "agent") can comprise, among other things, a drug made from one or any combination of the following or their equivalents, derivatives or analogs, including, anti-glaucoma medications, (e.g. adrenergic agonists, adrenergic antagonists (beta blockers), carbonic anhydrase inhibitors (CAIs, systemic and topical), parasympathomimetics, prostaglandins and hypotensive lipids, and combinations thereof), antimicrobial agent (e.g., antibiotic, antiviral, antiparacytic, antifungal, etc.), a corticosteroid or other anti-inflammatory (e.g., an NSAID or other analgesic and pain management compounds), a decongestant (e.g., vasoconstrictor), an agent that prevents of modifies an allergic response (e.g., an antihistamine, cytokine inhibitor, leucotriene inhibitor, IgE inhibitor, immunomodulator), a mast cell stabilizer, cycloplegic or the like.

Example agents include, but are not limited to, thrombin inhibitors; antithrombogenic agents; thrombolytic agents; fibrinolytic agents; vasospasm inhibitors; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triamcinolone, triamcinolone acetonide); non steroidal anti-inflammatories (NSAIDs) (such as salicylate, indomethacin, ibuprofen, diclofenac, flurbiprofen, piroxicam indomethacin, ibuprofen, naxopren, piroxicam and nabumetone). Examples of such anti-inflammatory steroids contemplated for use with the present lacrimal implants, include triamcinolone acetonide (generic name) and corticosteroids that include, for example, triamcinolone, dexamethasone, fluocinolone, cortisone, prednisolone, flumetholone, and derivatives thereof.); antiallergenics (such as sodium chromoglycate, antazoline, methapyriline, chlorpheniramine, cetrizine, pyrilamine, prophenpyridamine); anti proliferative agents (such as 1,3-cis retinoic acid, 5-fluorouracil, taxol, rapamycin, mitomycin C and cisplatin); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); antineoplastics (such as carmustine, cisplatin, fluorouracil3; immunological drugs (such as vaccines and immune stimulants); hormonal agents (such as estrogens, estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotrapin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix; components; ACE inhibitors; free radical scavengers; chelators; antioxidants; anti polymerases; photodynamic therapy agents; gene therapy agents; and other therapeutic agents such as prostaglandins, antiprostaglandins, prostaglandin precursors, including antiglaucoma drugs including beta-blockers such as Timolol, betaxolol, levobunolol, atenolol, and prostaglandin analogues such as Bimatoprost, travoprost, latanoprost etc; carbonic anhydrase inhibitors such as acetazolamide, dorzolamide, brinzolamide, methazolamide, dichlorphenamide, diamox; and neuroprotectants such as lubezole, nimodipine and related compounds; and parasympathomimetrics such as pilocarpine, carbachol, physostigmine and the like.

Additional agents that can be used with the present lacrimal implants include, but are not limited to, drugs that have been approved under Section 505 of the United States Federal Food, Drug, and Cosmetic Act or under the Public Health Service Act, some of which can be found at the U.S. Food and Drug Administration (FDA) website http://www.accessdata.fda.gov/scripts/cder/drugsatfda/index. The present lacrimal implants can also be used with drugs listed in the Orange Book, either in paper or in electronic form, which can be found at the FDA Orange Book website (http://www-.fda.gov/cder/ob/)), that has or records the same date as, earlier date than, or later date than, the filing date of this patent document. For example, these drugs can include, among others, dorzolamide, olopatadine, travoprost, bimatoprost, cyclosporin, brimonidine, moxifloxacin, tobramycin, brinzolamide, aciclovir timolol maleate, ketorolac tromethamine, prednisolone acetate, sodium hyaluronate, nepafenac, bromfenac, diclofenac, flurbiprofen, suprofenac, binoxan, patanol, dexamethasone/tobramycin combination, moxifloxacin, or acyclovir.

Examples of conditions that can be treated with the agent(s) include, but are not limited to, glaucoma, pre- and post-surgical ocular treatments, dry eye and allergies. In some examples, the therapeutic agent can include a lubricant or a surfactant, for example a lubricant to treat dry eye. In other examples, the therapeutic agent can include an absorbent capable of absorbing tear from an eye.

Drug Core Examples:

The drug core can comprise the agent(s) and in some examples one or more materials to provide sustained release of the agent(s). The agent migrates from the drug core to the target tissue, for example, to ciliary muscles of the eye. The agent can optionally be only slightly soluble in the matrix so that a small amount of agent is dissolved in the matrix and available for release from the surface of drug core. As the agent diffuses or otherwise migrates from the exposed surface of the core to the tear or tear film, the rate of migration from the core to the tear or tear film can be related to the concentration of agent dissolved in the matrix. In addition or in combination, the rate of migration of agent from the core to the tear or tear film can be related to one or more properties of the matrix in which the agent dissolves. In some examples, the rate of migration from the drug core to the tear or tear film can be based on a silicone formulation. In some examples, the concentration of agent dissolved in the drug core can be controlled to provide the desired rate of release of the agent. In some examples, the agent included in the core can include liquid, solid, solid gel, solid crystalline, solid amorphous, solid particulate, or dissolved forms of the therapeutic agent. The agent can comprise liquid or solid inclusions, for example liquid latanoprost droplets or solid Bimatoprost particles, respectively, dispersed in a silicone matrix.

The drug core can comprise one or more biocompatible materials capable of providing a sustained release of the agent. Although the drug core is primarily discussed above with respect to an example comprising a matrix with a substantially non-biodegradable silicone matrix with dissolvable inclusions of the drug located therein, the drug core can include other structures that provide sustained release of the agent, for example a biodegradable matrix, a porous drug core, a liquid drug core or a solid drug cores. A matrix that includes the agent can be formed from either biodegradable or non-biodegradable polymers. In some examples, a non-biodegradable drug core can include silicone, acrylates, polyethylenes, polyurethane, polyurethane, hydrogel, polyester (e.g., DACRON® from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, silicone rubber, polyethylene terephthalate, ultra high molecular weight polyethylene, polycarbonate urethane, polyurethane, polyimides, stainless steel, nickel-titanium alloy (e.g., Nitinol), titanium, stainless steel, cobalt-chrome alloy (e.g., ELGILOY® from Elgin Specialty Metals, Elgin, Ill.; CONICHROME® from Carpenter Metals Corp., Wyomissing, Pa.). In some examples, a biodegradable drug core can comprise one or more biodegradable polymers, such as protein, hydrogel, polyglycolic acid (PGA), polylactic acid (PLA), poly(L-lactic acid) (PLLA), poly(L-glycolic acid) (PLGA), polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid) and combinations thereof. In some examples, the drug core can comprise at least one of hydrogel polymer.

EXPERIMENTAL EXAMPLES

In order that the present lacrimal implants can be more fully understood, the following examples are given by way of illustration.

Experimental Example 1

Figure 12:
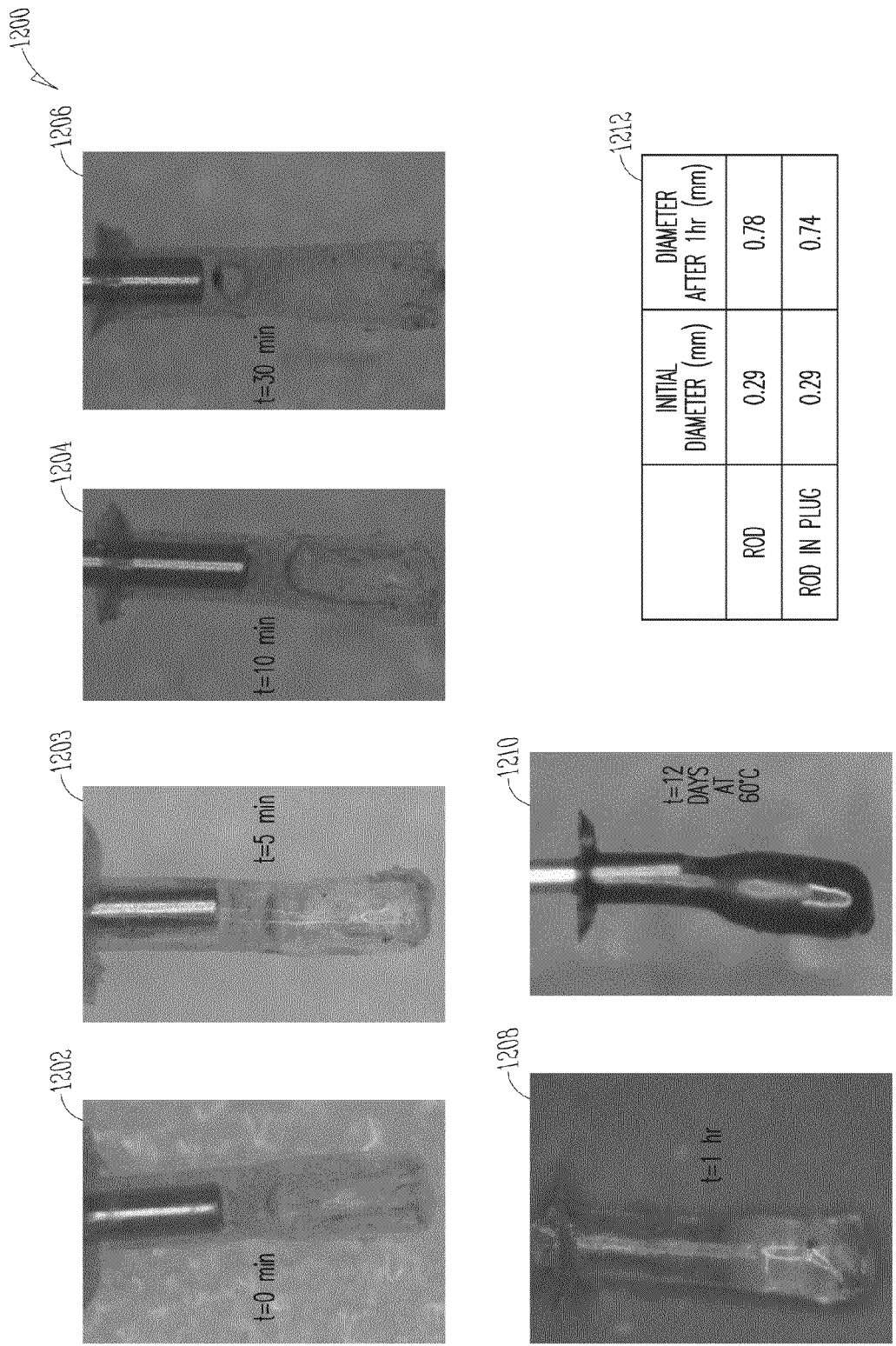
FIGS. 12-18 illustrate and chart example experimental results of a present lacrimal implant.

FIG. 12 illustrates a lacrimal implant 1200 comprising a implant body, which includes a retention structure. In this example, the retention structure is encapsulating an Oasis hydrogel retention element. To allow fluid to be received by the Oasis hydrogel retention element, the retention structure includes a fluid permeable retainer in the form of a silicone/contact lens hydrophilic cap member. In this example, the cap member includes 80% silicone and 20% contact lens material (Vista Optics 75). In addition to allowing the receipt of fluid into the retention structure, the silicone/contact lens cap member further inhibits the Oasis hydrogel from protruding out of the retention structure during expansion.

At 1202, the Oasis hydrogel and the encapsulating retention structure is shown at t=0 min. At 1203, the Oasis hydrogel and the encapsulating retention structure is shown at t=5 min. At 1204, the Oasis hydrogel and the encapsulating retention structure is shown at t=10 min. At 1206, the Oasis hydrogel and the encapsulating retention structure is shown at t=30 min. At 1208, the Oasis hydrogel and the encapsulating retention structure is shown at t=1 hr. At 1210, the Oasis hydrogel and the encapsulating retention structure is shown at t=12 days at 60° C. Table 1212 shows that the Oasis hydrogel retention element increased in size from an initial diameter of 0.29 millimeters to an expanded diameter of 0.78 millimeters during a 1 hr. time period; and further shows that the Oasis hydrogel retention element in the implant increased in size from an initial diameter of 0.29 millimeters to an expanded diameter of 0.74 millimeters during a 1 hr. time period.

Experimental Example 2

Figure 13:
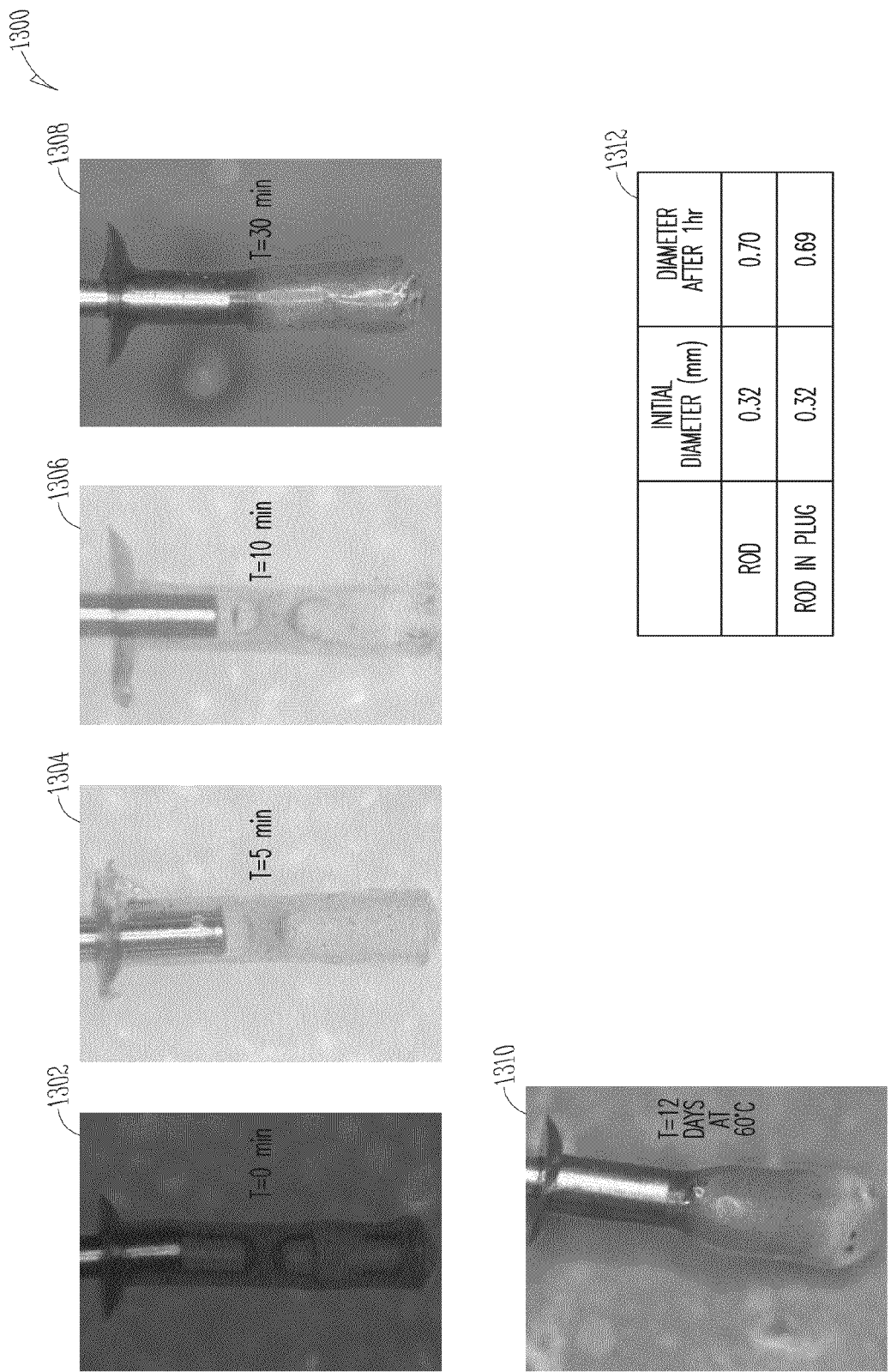

FIG. 13 illustrates a lacrimal implant 1300 comprising a implant body, which includes a retention structure. In this example, the retention structure is encapsulating a TG-2000 hydrogel retention element. To allow fluid to be received by the TG-2000 hydrogel retention element, the retention structure includes a fluid permeable retainer in the form of a silicone/contact lens hydrophilic cap member. In this example, the cap member includes 80% silicone and 20% contact lens material (Vista Optics 75). In addition to allowing the receipt of fluid into the retention structure, the silicone/contact lens cap member further inhibits the TG-2000 hydrogel from protruding out of the retention structure during expansion.

At 1302, the TG-2000 hydrogel and the encapsulating retention structure is shown at t=0 min. At 1304, the TG-2000 hydrogel and the encapsulating retention structure is shown at t=5 min. At 1306, the TG-2000 hydrogel and the encapsulating retention structure is shown at t=10 min. At 1308, the TG-2000 hydrogel and the encapsulating retention structure is shown at t=30 min. At 1310, the TG-2000 hydrogel and the encapsulating retention structure is shown at t=12 days at 60° C. Table 1312 shows that the TG-2000 hydrogel retention element increased in size from an initial diameter of 0.32 millimeters to an expanded diameter of 0.70 millimeters during a 1 hr. time period; and further shows that the TG-2000 hydrogel retention element in the implant increased in size from an initial diameter of 0.32 millimeters to an expanded diameter of 0.69 millimeters during a 1 hr. time period.

Experimental Example 3

Figure 14:
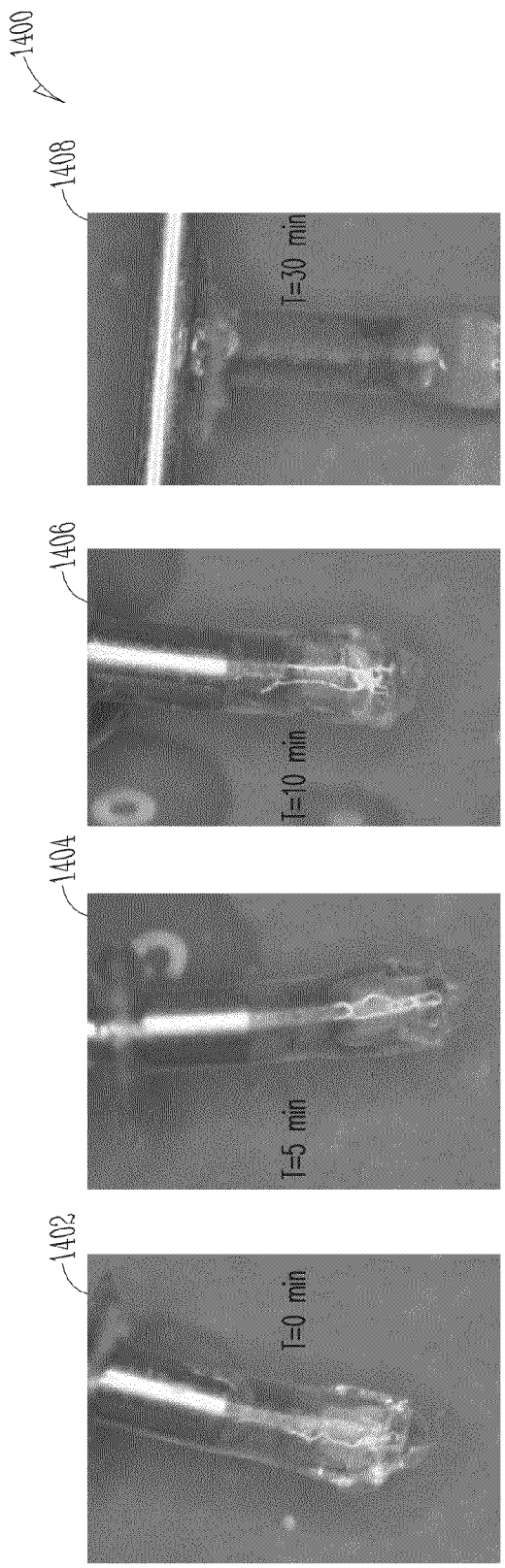
Figure 14:
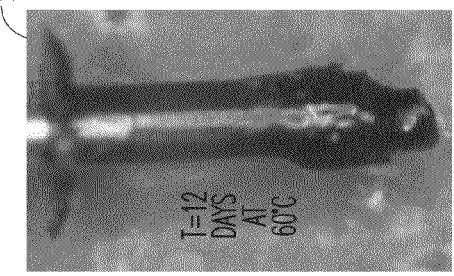

FIG. 14 illustrates a lacrimal implant 1400 comprising a implant body, which includes a retention structure. In this example, the retention structure is encapsulating a Contamac-78% hydrogel retention element. To allow fluid to be received by the Contamac-78% hydrogel retention element, the retention structure includes a fluid permeable retainer in the form of a silicone/contact lens hydrophilic cap member. In this example, the cap member includes 80% silicone and 20% contact lens material (Vista Optics 75). In addition to allowing the receipt of fluid into the retention structure, the silicone/contact lens cap member further inhibits the Contamac-78% hydrogel from protruding out of the retention structure during expansion.

At 1402, the Contamac-78% hydrogel and the encapsulating retention structure is shown at t=0 min. At 1404, the Contamac-78% hydrogel and the encapsulating retention structure is shown at t=5 min. At 1406, the Contamac-78% hydrogel and the encapsulating retention structure is shown at t=10 min. At 1408, the Contamac-78% hydrogel and the encapsulating retention structure is shown at t=30 min. At 1410, the Contamac-78% hydrogel and the encapsulating retention structure is shown at t=12 days at 60° C. Table 1412 shows that the Contamac-78% hydrogel retention element increased in size from an initial diameter of 0.27 millimeters to an expanded diameter of 0.46 millimeters during a 1 hr. time period; and further shows that the Contamac-78% hydrogel retention element in the implant increased in size from an initial diameter of 0.27 millimeters to an expanded diameter of 0.48 millimeters during a 1 hr. time period.

Experimental Example 4

Figure 15:
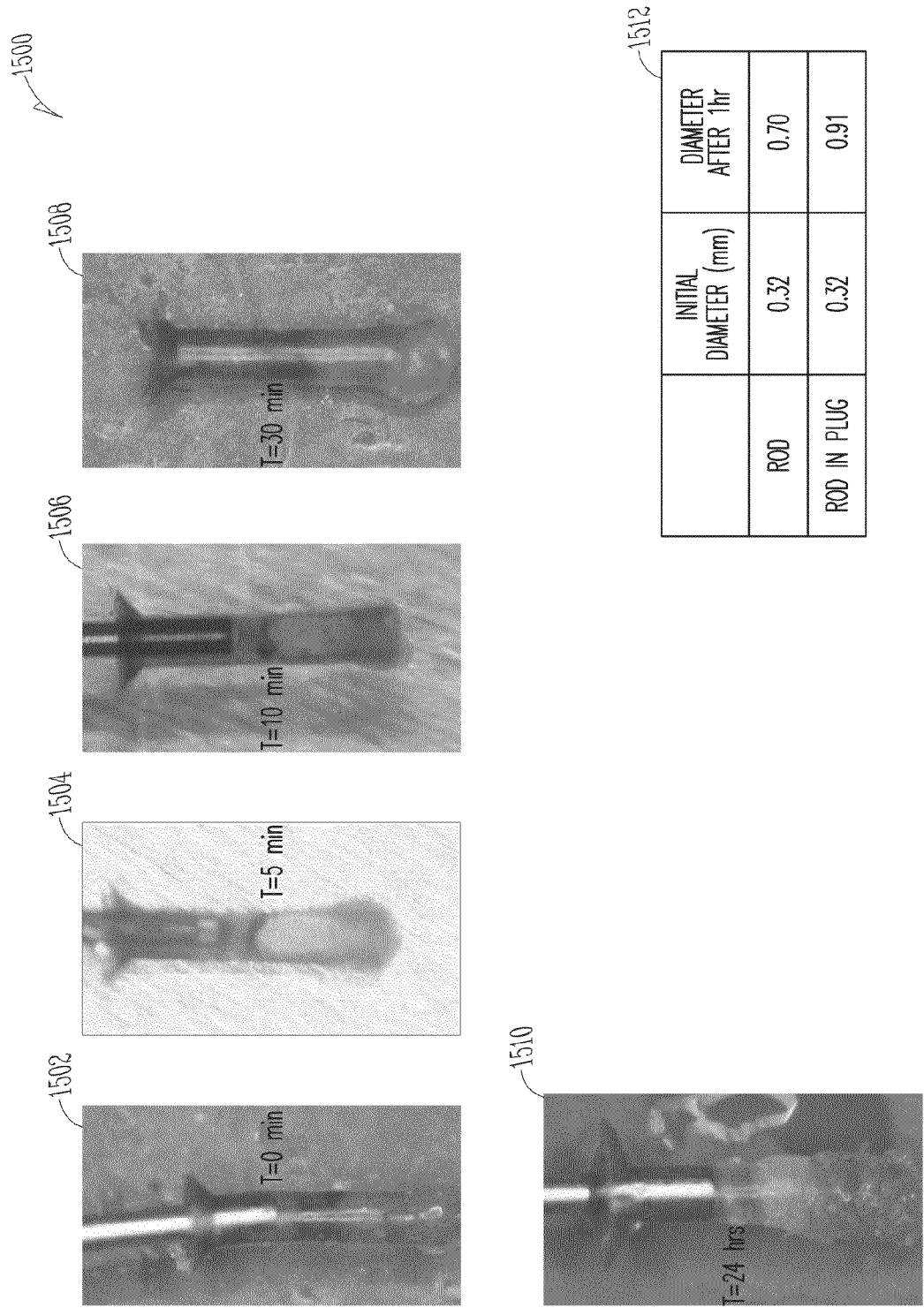

FIG. 15 illustrates a lacrimal implant 1500 comprising a implant body, which includes a retention structure. In this example, the retention structure is encapsulating a TG-2000 hydrogel retention element. To allow fluid to be received by the TG-2000 hydrogel retention element, the retention structure includes a fluid permeable retainer in the form of a silicone/salt hydrophilic cap member. In this example, the cap member includes 60% silicone and 40% salt (NaCl). In addition to allowing the receipt of fluid into the retention structure, the silicone/salt cap member further inhibits the TG-2000 hydrogel from protruding out of the retention structure during expansion.

At 1502, the TG-2000 hydrogel and the encapsulating retention structure is shown at t=0 min. At 1504, the TG-2000 hydrogel and the encapsulating retention structure is shown at t=5 min. At 1506, the TG-2000 hydrogel and the encapsulating retention structure is shown at t=10 min. At 1508, the TG-2000 hydrogel and the encapsulating retention structure is shown at t=30 min. At 1510, the TG-2000 hydrogel and the encapsulating retention structure is shown at t=12 days at 60° C. Table 1512 shows that the TG-2000 hydrogel retention element increased in size from an initial diameter of 0.32 millimeters to an expanded diameter of 0.70 millimeters during a 1 hr. time period; and further shows that the TG-2000 hydrogel retention element in the implant increased in size from an initial diameter of 0.32 millimeters to an expanded diameter of 0.91 millimeters during a 1 hr. time period.

Experimental Example 5

Figure 16:
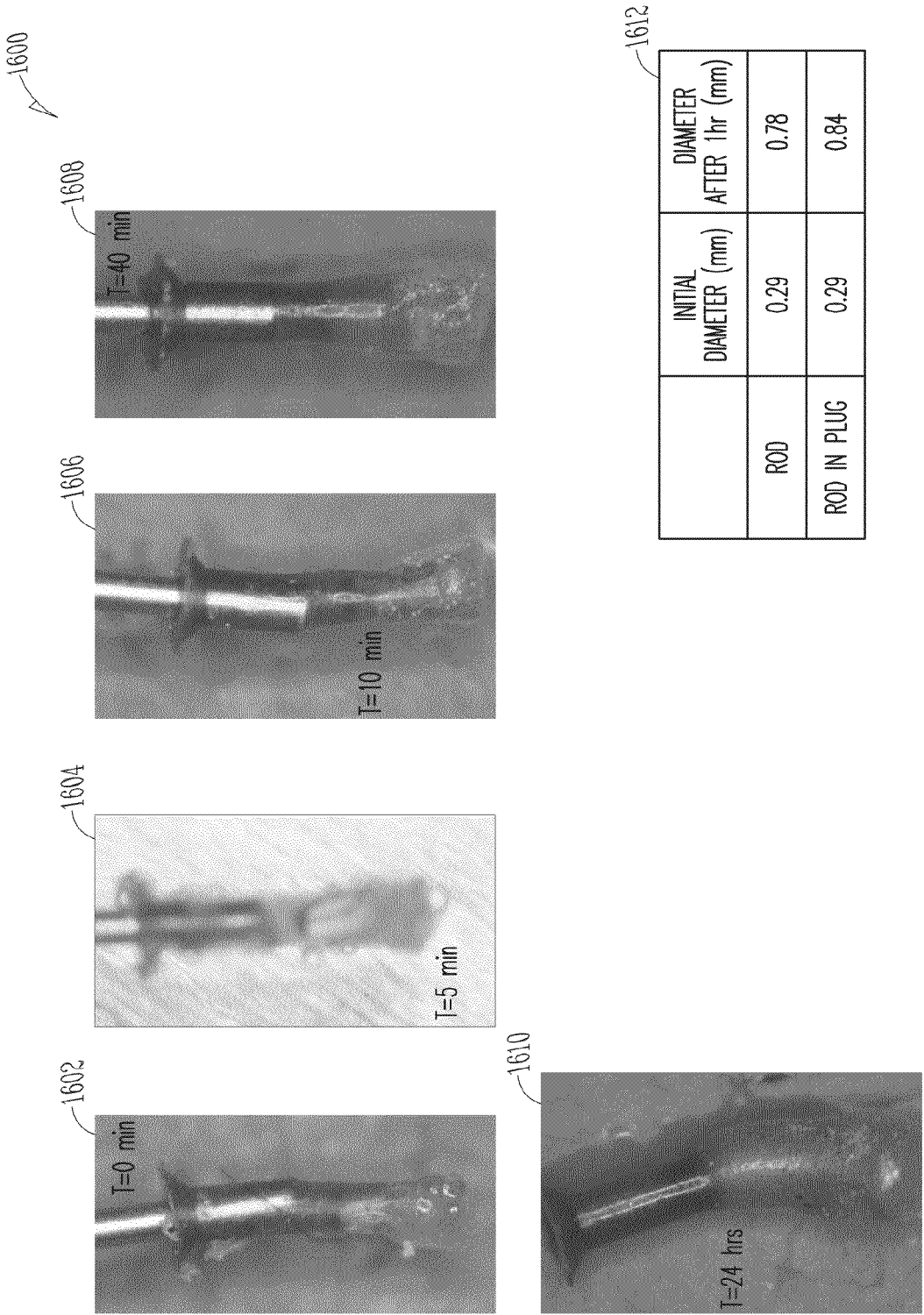

FIG. 16 illustrates a lacrimal implant 1600 comprising a implant body, which includes a retention structure. In this example, the retention structure is encapsulating an Oasis hydrogel retention element. To allow fluid to be received by the Oasis hydrogel retention element, the retention structure includes a fluid permeable retainer in the form of a silicone/salt hydrophilic cap member. In this example, the cap member includes 60% silicone and 40% salt (NaCl). In addition to allowing the receipt of fluid into the retention structure, the silicone/salt cap member further inhibits the Oasis hydrogel from protruding out of the retention structure during expansion.

At 1602, the Oasis hydrogel and the encapsulating retention structure is shown at t=0 min. At 1604, the Oasis hydrogel and the encapsulating retention structure is shown at t=5 min. At 1606, the Oasis hydrogel and the encapsulating retention structure is shown at t=10 min. At 1608, the Oasis hydrogel and the encapsulating retention structure is shown at t=30 min. At 1610, the Oasis hydrogel and the encapsulating retention structure is shown at t=12 days at 60° C. Table 1612 shows that the Oasis hydrogel retention element increased in size from an initial diameter of 0.29 millimeters to an expanded diameter of 0.78 millimeters during a 1 hr. time period; and further shows that the Oasis hydrogel retention element in the implant increased in size from an initial diameter of 0.29 millimeters to an expanded diameter of 0.84 millimeters during a 1 hr. time period.

Experimental Example 6

Figure 17:
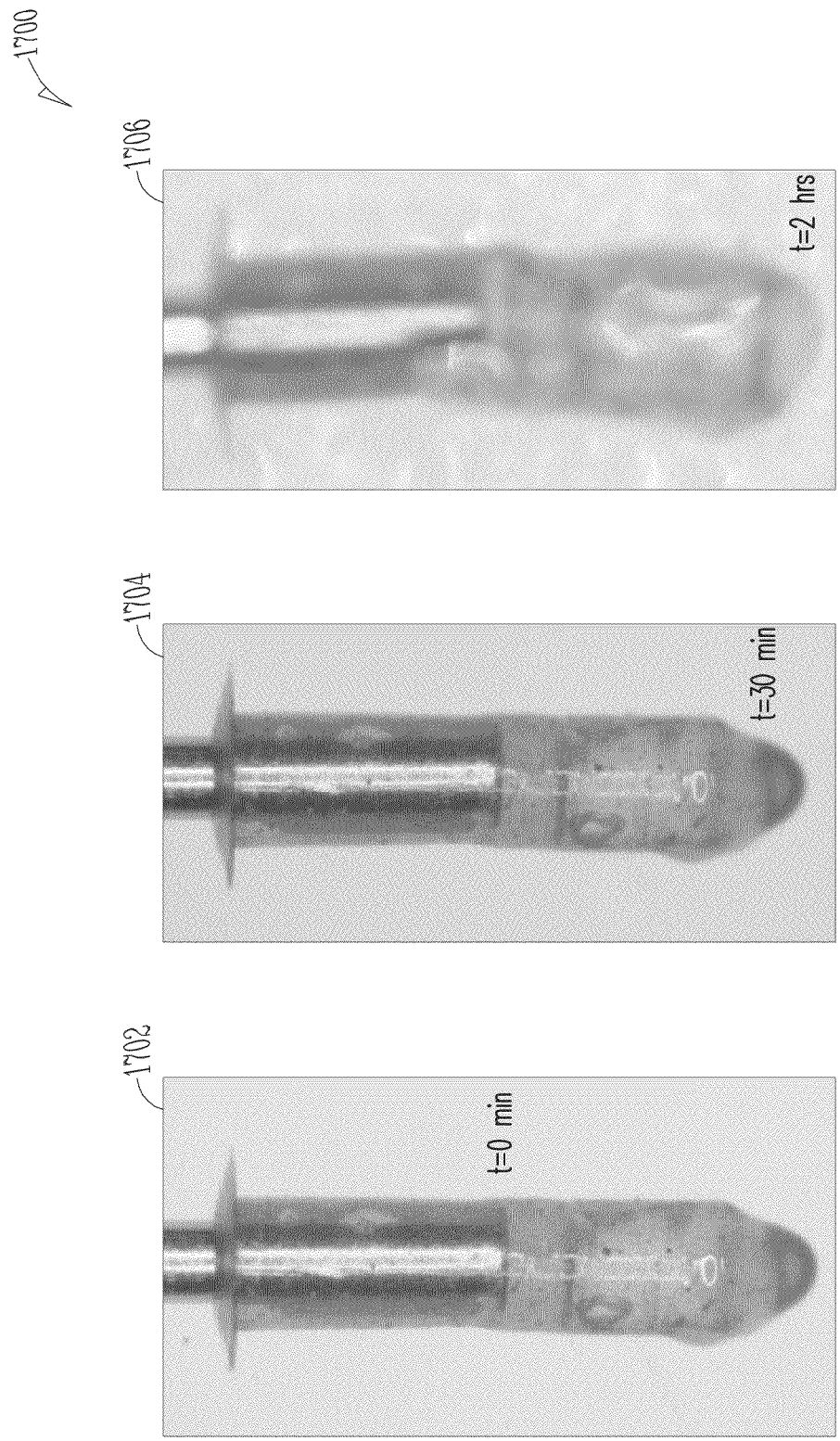

FIG. 17 illustrates a lacrimal implant 1700 comprising a implant body, which includes a retention structure. In this example, the retention structure is encapsulating a TG-2000 hydrogel retention element. To allow fluid to be received by the TG-2000 hydrogel retention element, the retention structure includes a fluid permeable retainer in the form of a silicone/cross-linked poly(1-(2-oxo-1-pyrrolidinyl)ethylene (PVP) hydrophilic cap member. In this example, the cap member includes 70% silicone and 30% cross-linked PVP (Povidone®) having a molecular weight of 111.14). In addition to allowing the receipt of fluid into the retention structure, the silicone/cross-linked PVP cap member further inhibits the TG-2000 hydrogel from protruding out of the retention structure during expansion.

At 1702, the TG-2000 hydrogel and the encapsulating retention structure is shown at t=0 min. At 1704, the TG-2000 hydrogel and the encapsulating retention structure is shown at t=30 min. At 1706, the TG-2000 hydrogel and the encapsulating retention structure is shown at t=2 hr.

Experimental Example 7

Figure 18:
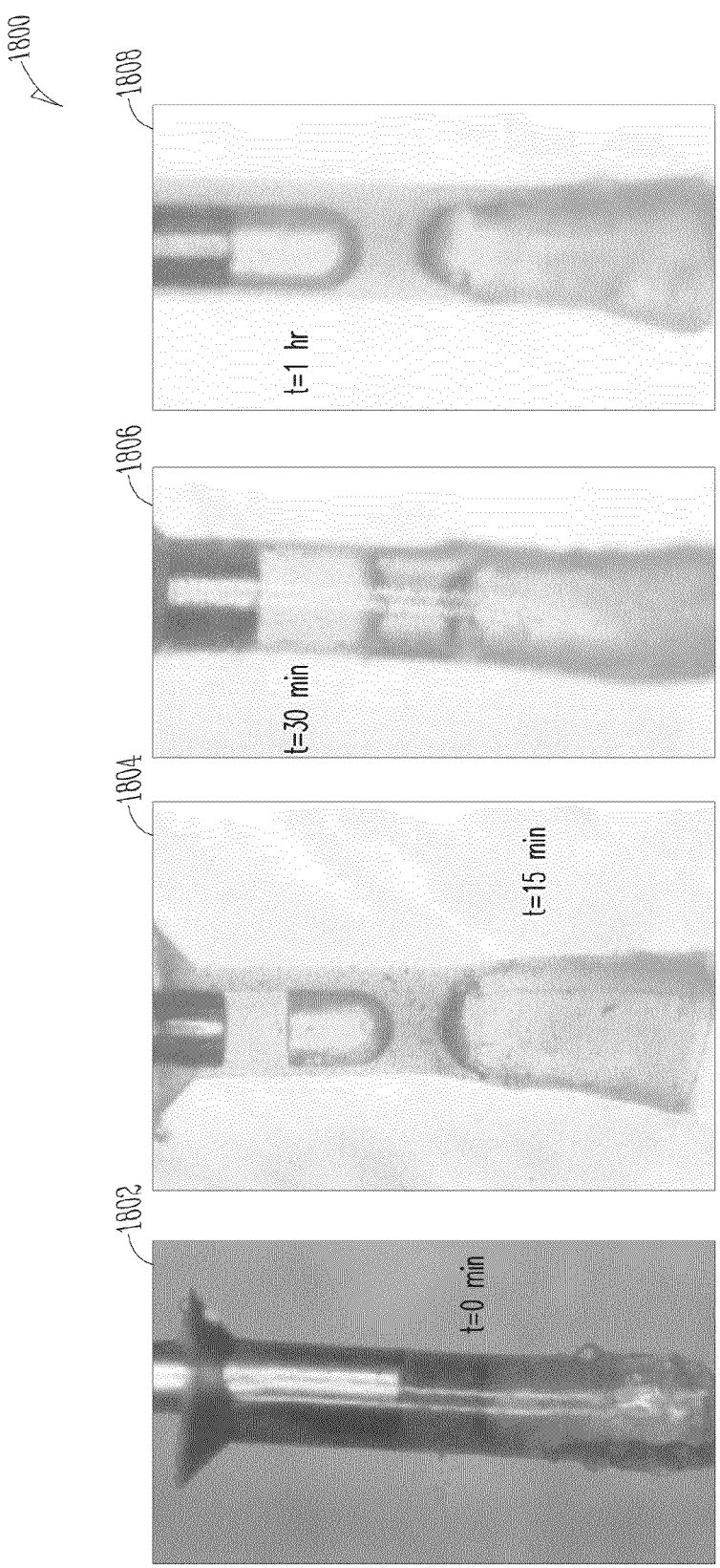

FIG. 18 illustrates a lacrimal implant 1800 comprising a implant body, which includes a retention structure. In this example, the retention structure is encapsulating a TG-2000 hydrogel retention element. To allow fluid to be received by the TG-2000 hydrogel retention element, the retention structure includes a fluid permeable retainer in the form of a silicone/poly(ethylene oxide) (PEO) hydrophilic cap member. In this example, the cap member includes 75% silicone and 25% PEO (having a molecular weight of 8,000,000 daltons). In addition to allowing the receipt of fluid into the retention structure, the silicone/PEO cap member further inhibits the TG-2000 hydrogel from protruding out of the retention structure during expansion.

At 1802, the TG-2000 hydrogel and the encapsulating retention structure is shown at t=0 min. At 1804, the TG-2000 hydrogel and the encapsulating retention structure is shown at t=15 min. At 1806, the TG-2000 hydrogel and the encapsulating retention structure is shown at t=30 hr. At 1808, the TG-2000 hydrogel and the encapsulating retention structure is shown at t=1 hr.

Closing Notes:

Among other things, lacrimal implants and related methods providing secure retention within a lacrimal canaliculus of an eye are discussed herein. The lacrimal implants can comprise a implant body configured for at least partial insertion through a punctum and into the lacrimal canaliculus. The implant body can include a retention structure configured to substantially encapsulate an expandable retention element. Accordingly, as the retention element expands, at least one outer surface portion of the retention structure is urged outward against a wall of the lacrimal canaliculus. In various examples, the lacrimal implant can further comprise a drug core insertable into the implant body to provide sustained release of an agent to the eye.

Advantageously, in some examples, the present lacrimal implants can successfully block the flow of tears or provide sustained delivery of a therapeutic agent to the eye for varying periods of time, such as from days to months to years. In addition, by substantially encapsulating the expandable retention element using the implant body, portions of the retention element (including outlying portions) are inhibited from separating from the rest of the implant allowing for cleaner removal and possibly enhanced implant retainment. Further, the expandable nature of the retention element allows for easier implantation, as much of the retention element expansion is configured to occur when the implant is implanted as desired. Even further, it is believe the present lacrimal implants can be implemented so as to provide a one-size-fits-all regime, as the expandable nature of the retention element permits the implant to fit in hollow tissue structures of varying sizes.

The above Detailed Description includes references to the accompanying drawings, which form a part of the Detailed Description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable Inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the term "about" is used to refer to an amount that is approximately, nearly, almost, or in the vicinity of being equal to a stated amount.

In this document, the term "hydrogel" is used to refer to an absorbing or otherwise retaining material (e.g., adsorbing material), such as super-absorbent polymers, hydrocolloids, and water-absorbent hydrophilic polymers, for example. In some examples, the term "hydrogel" refers to super-absorbent polymer particles in a "dry" state, more specifically, particles containing from no water up to an amount of water less than the weight of the particles, such as less than about 5%, by weight, water. In some examples, the term "hydrogel" also refers to a super-absorbent polymer in the "dry" state when the hydrogel is not expandable and also refers to its hydrated or expanded state, more specifically, hydrogels that have absorbed at least their weight in water, such as several times their weight in water. As the hydrogel material absorbs fluid, it size can increase and its shape can change to urge portions of a retention structure outward, such as against a wall of a lacrimal canaliculus, for example.

In this document, the terms "substantially encapsulating" are used to refer to an arrangement in which an element is surrounded by a structure such that at least 90% of the element outer surface area is enclosed. In some examples, the terms "substantially encapsulating" are used to refer to an arrangement in which an element is surrounded by a structure such that at least 95% of the element outer surface area is enclosed. In some examples, the terms "substantially encapsulating" are used to refer to an arrangement in which an element is surrounded by a structure such that at least 98% of the element outer surface area is enclosed.

In the appended claims, the terms "including" and "in which" are used as the plain-English equivalents of the respective terms "comprising" and "wherein." Also, in the following claims, the terms "including" and "comprising" are open-ended, that is, a system, assembly, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more features thereof) can be used in combination with each other. Other embodiments can be used, such as by one of ordinary skill in the art upon reviewing the above description. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The Abstract is provided to comply with 37 C.F.R. §1.72 (b), to allow the reader to quickly ascertain the nature of the technical disclosure. It is submitted with the understanding that it will not be used to interpret or limit the scope or meaning of the claims.

What is claimed is:

1. A lacrimal implant insertable through a lacrimal punctum, the lacrimal implant comprising:
  a drug insert, an expandable retention element and a unitary implant body extending from a proximal end portion, positionable adjacent to the lacrimal punctum, to a distal end portion, positionable in a lacrimal canaliculus, the implant body comprising a first chamber configured to house the drug insert, a second chamber configured to house the expandable retention element, and an intermediate portion positioned between the first and second chamber;
  wherein the drug insert comprises a drug core comprising a therapeutic agent dispersed in a matrix and an impermeable sheath body partially covering the drug core configured to provide at least one exposed drug core surface at a proximal end of the lacrimal implant;
  wherein the expandable retention element is configured to expand in at least one direction when the lacrimal implant is implanted in a lacrimal canaliculus to retain the implant body in the lacrimal canaliculus,
  and wherein the intermediate portion of the implant body is configured to inhibit communication of material between the first and second chamber.

2. The lacrimal implant of claim 1, wherein the expandable retention element comprises a fluid absorbing material having an expansion capacity of about 1 time its unexpanded volume.

3. The lacrimal implant of claim 1, wherein the expandable retention element comprises a fluid absorbing material having an expansion capacity of up to about 10 times its unexpanded volume.

4. The lacrimal implant of claim 1, wherein the expandable retention element comprises a substantially non-fluid absorbing material.

5. The lacrimal implant of claim 4, wherein the non-fluid absorbing material includes a shape-memory thermoplastic.

6. The lacrimal implant of claim 4, wherein the non-fluid absorbing material includes an oxide generating system configured to generate and release a plurality of oxides within the second chamber when implanted in the lacrimal canaliculus.

7. The lacrimal implant of claim 1, wherein at least a portion of a distal end of the implant body comprises a fluid permeable or hydrophilic material.

8. The lacrimal implant of claim 7, wherein the fluid permeable or hydrophilic material includes at least about 50 wt. % silicone in combination with at least one hydrophilic polymer selected from the group consisting of: a contact lens material, sodium chloride, polyethylene oxide, polyethylene glycol, polyvinyl pyrilidone, polyvinyl alcohol, and any combination thereof.

9. The lacrimal implant of claim 7, wherein the fluid permeable or hydrophilic material is disposed at a lateral surface exposable to fluid when the implant body is implanted in the lacrimal canaliculus.

10. The lacrimal implant of claim 1, wherein the second chamber includes a fluid permeable or hydrophilic cap member coupled to the distal end portion of the implant body.

11. The lacrimal implant of claim 10, wherein the cap member includes a tapered distal tip portion configured to facilitate atraumatic insertion through the lacrimal punctum.

12. The lacrimal implant of claim 1, wherein the second chamber inhibits at least about 80% of the expandable retention element from protruding out of the implant body.

13. The lacrimal implant of claim 1, wherein the implant body comprises a fluid permeable aperture, the fluid permeable aperture having a size and shape allowing fluid into the second chamber and further inhibiting the expandable retention element from protruding out of the implant body during expansion.

14. The lacrimal implant of claim 13, wherein the size and shape of the fluid permeable aperture is configured to inhibit the escape of the expandable retention element such that expulsion thereof is limited to less than 5% of an expanded retention element volume.

15. The lacrimal implant of claim 13, wherein the size and shape of the fluid permeable aperture comprises a diameter up to about 0.3 millimeters.

16. The lacrimal implant of claim 13, comprising an aperture membrane configured to cover the fluid permeable aperture, the aperture membrane disposed on an interior or an exterior of the implant body and having a molecular weight of 10,000 daltons or less.

17. The lacrimal implant of claim 1, wherein the at least one exposed drug core surface is disposed at or near the proximal end portion of the implant body to contact a tear fluid and release the therapeutic agent over a sustained period when the implant body is inserted through the lacrimal punctum.

18. The lacrimal implant of claim 1, comprising an implant body projection extending at least partially from or around the proximal end portion of the implant body, and configured to seat against the lacrimal punctum.

19. The lacrimal implant of claim 1, wherein the implant body is configured to be completely insertable through the lacrimal punctum.

20. The lacrimal implant of claim 1, comprising a fluid swellable material disposed on an outer surface portion of the implant body, the fluid swellable material providing secondary retention of the implant body within the lacrimal canaliculus.

21. The lacrimal implant of claim 1, configured in a kit for treating an eye disease, in combination with instructions for using the lacrimal implant to treat an eye disorder.

22. The lacrimal implant of claim 1, wherein the material comprises fluid.

23. The lacrimal implant of claim 1, wherein the expandable retention element is formed separately from the implant body and inserted into the chamber upon assembly of the lacrimal implant.

24. A method of treating a subject having an eye disorder, comprising:
   releasing a drug using a lacrimal implant that has been inserted through at least one lacrimal punctum of the subject, the lacrimal implant comprising,
   a drug insert, an expandable retention element and a unitary implant body extending from a proximal end portion, positionable adjacent to the lacrimal punctum, to a distal end portion, positionable in a lacrimal canaliculus, the implant body comprising a first chamber configured to house the drug insert, a second chamber configured to house the expandable retention element, and an intermediate portion positioned between the first and second chamber;
   wherein the drug insert comprises a drug core comprising a therapeutic agent dispersed in a matrix and an impermeable sheath partially covering the drug core configured to provide at least one exposed drug core surface at a proximal end of the lacrimal implant,
   the expandable retention element configured to expand when the implant body is implanted in a lacrimal canaliculus to retain the implant body in the lacrimal canaliculus.

25. The method of claim 24, wherein the eye disorder is a glaucoma disease.

26. The method of claim 25, wherein the glaucoma disease is ocular hypertension or primary open angle glaucoma.

27. The method of claim 24, wherein the drug core comprises an anti-glaucoma agent.

28. The method of claim 24, comprising replacing the lacrimal implant that has been inserted with a second lacrimal implant including at least one therapeutic agent inclusion following an interval of time.

29. The method of claim 24, wherein the expandable retention element is formed separately from the implant body and inserted into the chamber upon assembly of the lacrimal implant.

* * * * *